US010166522B2

(12) United States Patent
Hindson et al.

(10) Patent No.: US 10,166,522 B2
(45) Date of Patent: *Jan. 1, 2019

(54) SYSTEM FOR MIXING FLUIDS BY COALESCENCE OF MULTIPLE EMULSIONS

(71) Applicant: Bio-Rad Laboratories, Inc., Hercules, CA (US)

(72) Inventors: Benjamin J. Hindson, Livermore, CA (US); Billy W. Colston, Jr., San Ramon, CA (US); Kevin D. Ness, Pleasanton, CA (US); Donald A. Masquelier, Tracy, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 375 days.

This patent is subject to a terminal disclaimer.

(21) Appl. No.: 14/938,470

(22) Filed: Nov. 11, 2015

(65) Prior Publication Data

US 2016/0059204 A1   Mar. 3, 2016

Related U.S. Application Data

(63) Continuation of application No. 12/862,542, filed on Aug. 24, 2010, now Pat. No. 9,194,861.

(Continued)

(51) Int. Cl.
*C12Q 1/68* (2018.01)
*B01J 19/00* (2006.01)
(Continued)

(52) U.S. Cl.
CPC ....... *B01J 19/0046* (2013.01); *B01F 13/0071* (2013.01); *B01F 13/0079* (2013.01); *B01J 19/0093* (2013.01); *B01L 3/502784* (2013.01); *B01L 7/525* (2013.01); *C12Q 1/6844* (2013.01); *G01N 1/30* (2013.01); *G01N 1/44* (2013.01); *G01N 21/75* (2013.01); *G01N 33/50* (2013.01); *G01N 35/08* (2013.01); *B01J 2219/0059* (2013.01); *B01J 2219/00286* (2013.01); *B01J 2219/00418* (2013.01); *B01J 2219/00495* (2013.01); *B01J 2219/00599* (2013.01);
(Continued)

(58) Field of Classification Search
CPC combination set(s) only.
See application file for complete search history.

(56) References Cited

U.S. PATENT DOCUMENTS 3,575,220 A   4/1971   Davis et al.
4,051,025 A   9/1977   Ito
(Continued)

FOREIGN PATENT DOCUMENTS

EP   1 522 582 A2   4/2005
EP   1 522 582 B1   4/2007
(Continued)

OTHER PUBLICATIONS

European Patent Office, "Extended European Search Report" in connection with related European Patent Application No. 15157136.1, dated Sep. 8, 2015, 8 pages.
(Continued)

*Primary Examiner* — Teresa E Strzelecka
(74) *Attorney, Agent, or Firm* — Kolisch Hartwell, P.C.

(57) ABSTRACT

System, including methods, apparatus, compositions, and kits, for the mixing of small volumes of fluid by coalescence of multiple emulsions.

15 Claims, 7 Drawing Sheets

Related U.S. Application Data

(60) Provisional application No. 61/275,860, filed on Sep. 2, 2009.

(51) Int. Cl.

| | | |
|---|---|---|
| *G01N 21/75* | (2006.01) | |
| *C12Q 1/6844* | (2018.01) | |
| *G01N 33/50* | (2006.01) | |
| *B01F 13/00* | (2006.01) | |
| *B01L 3/00* | (2006.01) | |
| *G01N 35/08* | (2006.01) | |
| *B01L 7/00* | (2006.01) | |
| *G01N 1/30* | (2006.01) | |
| *G01N 1/44* | (2006.01) | |
| *C07H 21/02* | (2006.01) | |
| *C40B 50/08* | (2006.01) | |
| *C40B 60/14* | (2006.01) | |

(52) U.S. Cl.
CPC ........ *B01J 2219/00722* (2013.01); *B01J 2219/00873* (2013.01); *B01J 2219/00894* (2013.01); *B01J 2219/00903* (2013.01); *B01J 2219/00957* (2013.01); *B01L 2200/0673* (2013.01); *B01L 2200/16* (2013.01); *B01L 2300/0867* (2013.01); *B01L 2300/0883* (2013.01); *B01L 2300/18* (2013.01); *B01L 2400/0487* (2013.01); *B01L 2400/0677* (2013.01); *C40B 50/08* (2013.01); *C40B 60/14* (2013.01)

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 9,194,861 B2 | 11/2015 | Hindson et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |

(56) References Cited

U.S. PATENT DOCUMENTS

| | | |
|---|---|---|
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0044543 A1 | 2/2008 | McClements et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remade et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |

(56) References Cited

U.S. PATENT DOCUMENTS

| | | |
|---|---|---|
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| EP | 2473618 B1 | 3/2015 |
| GB | 1 503 163 | 3/1978 |
| GB | 2 097 692 | 11/1982 |
| JP | 0295433 | 4/1990 |
| JP | 2002-210354 | 7/2002 |
| JP | 2007-098322 | 4/2007 |
| JP | 2008-535644 | 9/2008 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2006096571 | 9/2006 |
| WO | 2007081387 A1 | 7/2007 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109878 | 9/2008 |
| WO | 2008/112177 | 9/2008 |
| WO | 2008109176 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

Scherer, Axel, California Institute of Technology, "Polymerase Chain Reactors" PowerPoint presentation, 24 pgs., date unknown.

Eschenbach Optik GMBH, Optics for Concentrated Photovoltaics (CPV), 1 pg., date unknown.

Canadian Intellectual Property Office, "Office Action" in connection with related Canadian Patent Application No. 2,767,056, dated Jun. 28, 2016, 4 pages.

Canadian Intellectual Property Office, "Office Action" in connection with related Canadian Patent Application No. 2,767,056, dated Jun. 9, 2017, 3 pages.

Maltezos, George Manuel, "Microfluidic Devices for Accesible Medical Diagnostics" thesis, Nov. 20, 2006, pp. 1-287.

3M Specialty Materials, "3M Fluorinert Electronic Liquid FC-3283," product information guide, issued Aug. 2001.

Abate, Adam R. et al., "Functionalized glass coating for PDMS microfluidic devices," Lab on a Chip Technology: Fabrication and Microfluidics, 11 pgs., (2009).

Abdelgawad, Mohamed et al., "All-terrain droplet actuation," Lab on a Chip, vol. 8, pp. 672-677, Apr. 2, 2008.

Alexandridis, Paschalis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Bransky, Avishay et al., "A microfluidic droplet generator based on a piezoelectric actuator," Lab on a Chip, vol. 9, pp. 516-520, Nov. 20, 2008.

Carroll, Nick J. et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.

Cawthon, Richard M., "Telomere length measurement by a novel monochrome multiplex quantitative PCR method," Nucleic Acids Research, vol. 37, No. 3, pp. 1-7, (2009).

Cawthon, Richard M., "Telomere measurement by quantitative PCR," Nucleic Acids Research, vol. 30, No. 10, pp. 1-6, (2002).

Chabert, Max et al., "Droplet fusion by alternating current (AC) field electrocoalescence in microchannels," Electrophoresis, vol. 26, pp. 3706-3715, (2005).

Chen, Chia-Hung et al., "Janus Particles Templated from Double Emulsion Droplets Generated Using Microfluidics," Langmuir, vol. 29, No. 8, pp. 4320-4323, Mar. 18, 2009.

Chen, Delai L. et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).

Chittofrati, A. et al., "Perfluoropolyether microemulsions," Progress in Colloid & Polymer Science 79, pp. 218-225, (1989).

Chloroform (Phenomenex), Solvent Miscibility Table, Internet Archive WayBackMachine, 3 pgs., Feb. 1, 2008.

Clausell-Tormos, Jenifer et al., "Droplet-Based Microfluidic Platforms for the Encapsulation and Screening of Mammalian Cells and Multicellular Organisms," Chemistry & Biology, vol. 15, pp. 427-437, May 2008.

Anna, Shelley L. et al., "Formation of dispersions using "flow focusing" in microchannels," Applied Physics Letters, vol. 82, No. 3, Jan. 20, 2003.

Avilion, Ariel A. et al., "Human Telomerase RNA and Telomerase Activity in Immortal Cell Lines and Tumor Tissues," Cancer Research 56, pp. 645-650, Feb. 1, 1996.

Baroud, Charles N. et al., "Thermocapillary valve for droplet production and sorting," Physical Review E 75, 046302, pp. 046302-1-046302-5, Apr. 5, 2007.

(56) References Cited

OTHER PUBLICATIONS

European Patent Office, "Supplementary European Search Report" in connection with related European Patent Application No. 10 814 252.2, dated Dec. 2012, 3 pages.
European Patent Office, "European Search Opinion" in connection with related European Patent Application No. 10 814 252.2, dated Dec. 2012, 8 pages.
Beer, N Reginald et al., "On-Chip, Real-Time, Single-Copy Polymerase Chain Reaction in Picoliter Droplets", Analytical Chemistry, vol. 79, No. 22, Nov. 15, 2007, pp. 8471-8475.
Beer, N. Reginald et al., "On-Chip Single-Copy Real-Time Reverse-Transcription PCR in Isolated Picoliter Droplets", Analytical Chemistry, vol. 80, No. 6, Mar. 15, 2008, pp. 1854-1858.
Beer, Neil Reginald et al., "Monodisperse droplet generation and rapid trapping for single molecule detection and reaction kinetics measurement," Lab on a Chip, vol. 9, pp. 841-844, Dec. 5, 2008.
Bhat, Somanath et al., "Effect of sustained elevated temperature prior to amplification on template copy number estimation using digital polymerase chain reaction," Analyst, vol. 136, pp. 724-732, (2011).
Blow, Nathan, "PCR's next frontier", Nature Methods, vol. 4, No. 10, Oct. 2007, pp. 869-875.
Fidalgo, Luis M. et al., "Coupling Microdroplet Microreactors with Mass Spectrometry: Reading the Contents of Single Droplets Online," Angewandte Chemie, vol. 48, pp. 3665-3668, Apr. 7, 2009.
Fielden, Peter et al., "Micro-Droplet Technology for High Throughout Systems and Methods," 1 pg., Mar. 8, 2006.
Garstecki, Piotr et al., "Formation of droplets and bubbles in a microfluidic T-junction—scaling and mechanism of break-up," Lab on a Chip, vol. 6, pp. 437-446, (2006).
Garstecki, Piotr et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Garti, N. et al., "Water Solubilization in Nonionic Microemulsions Stabilized by Grafted Siliconic Emulsifiers," Journal of Colloid and Interface Science vol. 233, pp. 286-294, (2001).
Gasperlin, M. et al., "The structure elucidation of semisolid w/o emulsion systems containing silicone surfactant," International Journal of Pharmaceutics 107, pp. 51-56, (1994).
Ge, Qinyu et al., "Emulsion PCR-based method to detect Y chromosome microdeletions," Analytical Biochemistry, vol. 367, pp. 173-178, May 10, 2007.
Ghenciu, E. G. et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Glotsos, Dimitris et al., "Robust Estimation of Bioaffinity Assay Fluorescence Signals," IEEE Transactions on Information Technology in Biomedicine, vol. 10, No. 4, pp. 733-739, Oct. 2006.
Goldschmidt GMBH, "Abil® EM 90 Emulsifier for the formulation of cosmetic W/O creams and lotions," degussa. creating essentials brochure, pp. 1-7, May 2003.
Da Rocha, Sandro R. P. et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Dasgupta, Purnendu K. et al., "Light emitting diode-based detectors Absorbance, fluorescence and spectroelectrochemical measurements in a planar flow-through cell," Analytica Chimica Acta 500, pp. 337-364, (2003).
Diehl, Frank et al., "Digital quantification of mutant DNA in cancer patients," Current Opinion in Oncology, vol. 19, pp. 36-42, (2007).
Diekema, Daniel J. et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Ding, Chunming et al., "Direct molecular haplotyping of long-range genomic DNA with M1-PCR," PNAS, vol. 100, No. 13, pp. 7449-7453, Jun. 24, 2003.
Dorfman, Kevin D. et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
Dressman, Devin et al., "Transforming single DNA molecules into fluorescent magnetic particles for detection and enumeration of genetic variations," PNAS, vol. 100, No. 15, Jul. 22, 2003.
Dube, Simant et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Emerson, David et al., "Microfluidic Modelling Activities at C3M," Centre for Microfluidics & Microsystems Modelling, Daresbury Laboratory, pp. 1-26, May 15, 2006.
Fan, Jian-Bing et al., "Highly parallel genomic assays," Nature Reviews/Genetics, vol. 7, pp. 632-644, Aug. 2006.
Hung, Lung-Hsin et al., "Rapid microfabrication of solvent-resistant biocompatible microfluidic devices," Lab on a Chip, vol. 8, pp. 983-987, Apr. 8, 2008.
Jarvius, Jonas et al., "Digital quantification using amplified single-molecule detection," Nature Methods, vol. 3, No. 9, pp. 15 pgs, Sep. 2006.
Jin, Dayong et al., "Practical Time-Gated Luminescence Flow Cytometry. II: Experimental Evaluation Using UV LED Excitation," Cytometry Part A • 71A, pp. 797-808, Aug. 24, 2007.
Kalinina, Olga et al., "Nanoliter scale PCR with TaqMan Detection," Nucleic Acids Research, vol. 25, No. 10 pp. 1999-2004, (1997).
Katsura, Shinji et al., "Indirect micromanipulation of single molecules in water-in-oil emulsion," Electrophoresis, vol. 22, pp. 289-293, (2001).
Kekevi, Burcu et al., Synthesis and Characterization of Silicone-Based Surfactants as Anti-Foaming Agents, J. Surfact Deterg (2012), vol. 15, pp. 73-81, published online Jul. 7, 2011.
Kim, Hanyoup et al., "Nanodroplet real-time PCR system with laser assisted heating", Optics Express, vol. 17, No. 1, Jan. 5, 2009, pp. 218-227.
Kiss, Margaret Macris et al., "High-Throughput Quantitative Polymerase Chain Reaction in Picoliter Droplets," Analytical Chemistry, 8 pgs., downloaded Nov. 17, 2008.
Kojima, Takaaki et al., "PCR amplification from single DNA molecules on magnetic beads in emulsion: application for high-throughput screening of transcription factor targets," Nucleic Acids Research, vol. 33, No. 17, pp. 1-9, (2005).
Kumaresan, Palani et al., "High-Throughput Single Copy DNA Amplification and Cell Analysis in Engineered Nanoliter Droplets," Analytical Chemistry, 17 pgs., Apr. 15, 2008.
Griffiths, Andrew D. et al., "Miniaturising the laboratory in emulsion droplets," TRENDS in Biotechnology, vol. 24, No. 9, pp. 395-402, Jul. 14, 2006.
Gullberg, Mats et al., "Cytokine detection by antibody-based proximity ligation," PNAS, vol. 101, No. 22, pp. 8420-8424, Jun. 1, 2004.
Guo, Zhen et al., "Enhanced discrimination of single nucleotide polymorphisms by artificial mismatch hybridization," Nature Biotechnology vol. 15, pp. 331-335, Apr. 1997.
Gustafsdottir, Sigrun M. et al., "In vitro analysis of DNA-protein interactions by proximity ligation," PNAS, vol. 104, No. 9, pp. 3067-3072, Feb. 27, 2007.
Higuchi, Russell et al., "Kinetic PCR Analysis: Real-time Monitoring of DNA Amplification Reactions," Bio/Technology vol. II, pp. 1026-1030, Sep. 11, 1993.
Hill, Randla M., "Silicone surfactants—new developments," Current Opinion in Colloid & Interface Science 7, pp. 255-261, (2002).
Hobbs, Helen R. et al., "Homogeneous Biocatalysis in both Fluorous Biphasic and Supercritical Carbon Dioxide Systems," Angewandte Chemie, vol. 119, pp. 8006-8009, Sep. 6, 2007.
Holtze, C. et al., "Biocompatible surfactants for water-in-fluorocarbon emulsions," Lab on a Chip, vol. 8, pp. 1632-1639, Sep. 2, 2008.
Hori, Machiko et al., "Uniform amplification of multiple DNAs by emulsion PCR," Biochemical and Biophysical Research Communications, vol. 352, pp. 323-328, (2007).

(56) References Cited

OTHER PUBLICATIONS

Huang, Jiaqi et al., "Rapid Screening of Complex DNA Samples by Single-Molecule Amplification and Sequencing," PLoS ONE, vol. 6, Issue 5, pp. 1-4, May 2011.

Markey, Amelia L. et al., "High-throughput droplet PCR," Methods, vol. 50, pp. 277-281, Feb. 2, 2010.

Mazutis, Linas et al., "A fast and efficient microfluidic system for highly selective one-to-one droplet fusion," Lab on a Chip, vol. 9, pp. 2665-2672, Jun. 12, 2009.

Mazutis, Linas et al., "Droplet-Based Microfluidic Systems for High-Throughput Single DNA Molecule Isothermal Amplification and Analysis", Analytical Chemistry, vol. 81, No. 12, Jun. 15, 2009, pp. 4813-4821.

McCaughan, Frank et al., "Single-molecule genomics," Journal of Pathology, vol. 220, pp. 297-306, Nov. 19, 2009.

Mehta, Somil C. et a., "Mechanism of Stabilization of Silicone Oil-Water Emulsions Using Hybrid Siloxane Polymers," Langmuir, vol. 24, No. 9, pp. 4558-4563, Mar. 26, 2008.

Mohr, S. et al., "Numerical and experimental study of a droplet-based PCR chip," Microfluid Nanofluid, vol. 3, pp. 611-621, (2007).

Musyanovych, Anna et al., "Miniemulsion Droplets as Single Molecule Nanoreactors for Polymerase Chain Reaction," Biomacromolecules, vol. 6, No. 4, pp. 1824-1828, (2005).

Nagai, Hidenori et al., "Development of a Microchamber Array for Picoliter PCR," Analytical Chemistry, vol. 73, No. 5, pp. 1043-1047, Mar. 1, 2001.

Nam, Yoon Sung et al., "Nanosized Emulsions Stabilized by Semisolid Polymer Interphase," Langmuir, ACS Publications, Jul. 23, 2010.

Newman, D.A., et al., "Phase Behavior of Fluoroether-Functional Amphiphiles in Supercritical Carbon Dioxide," The Journal of Supercritical Fluids, vol. 6, No. 4, pp. 205-210, (1993).

O'Lenick Jr., Anthony J. "Silicone Emulsions and Surfactants—A Review," Silicone Spectator, Silitech LLC, May 2009 (original published May 2000).

Kunieda, Hironobu et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Labsmith, "CapTite™ Microfluidic Interconnects" webpage, downloaded Jul. 11, 2012.

Labsmith, "Microfluid Components" webpage, downloaded Jul. 11, 2012.

Landegren, Ulf et al., "Padlock and proximity probes for in situ and array-based analyses: tools for the post-genomic era," Comp. Funct. Genom, vol. 4, pp. 525-530, (2003).

Leamon, John H. et al., "Overview: methods and applications for droplet compartmentalization of biology," Nature Methods, vol. 3, No. 7, pp. 541-543, Jul. 2006.

Lin, Yen-Heng et al., "Droplet Formation Utilizing Controllable Moving-Wall Structures for Double-Emulsion Applications," Journal of Microelectromechanical Systems, vol. 17, No. 3, pp. 573-581, Jun. 2008.

Link, Darren R. et al., "Electric Control of Droplets in Microfluidic Devices," Angewandte Chemie Int. Ed., vol. 45, pp. 2556-2560, (2006).

Liu, Kan et al., "Droplet-based synthetic method using microflow focusing and droplet fusion," Microfluid Nanfluid, vol. 3, pp. 239-243, (2007), published online Sep. 22, 2006.

Lo, Y. M. Dennis et al., "Digital PCR for the molecular detection of fetal chromosomal aneuploidy," PNAS, vol. 104, No. 32, pp. 13116-13121, Aug. 7, 2007.

Luk, Vivienne N. et al., "Pluronic Additives: A Solution to Sticky Problems in Digital Microfluidics," Langmuir, vol. 24, No. 12, pp. 6382-6289, May 16, 2008.

Margulies, Marcel et al., "Genome sequencing in microfabricated high-density picolitre reactors," Nature, vol. 437, 51 pgs., Sep. 15, 2005.

Japanese Patent Office, "Notice of Reasons for Rejection" in connection with related Japanese Patent Application No. 2012-527909, dated Nov. 17, 2014, 6 pages.

Schneegaß, Ivonne et al., "Miniaturized flow-through PCR with different template types in a silicon chip thermocycler," Lab on a Chip, vol. 1, pp. 42-49, (2001).

Schroeder, Groff M. et al., "Introduction to Flow Cytometry" version 5.1, 182 pgs. (2004).

Schütze, Tatjana et al., "A streamlined protocol for emulsion polymerase chain reaction and subsequent purification," Analytical Biochemistry, vol. 410, pp. 155-157, Nov. 25, 2010.

Sela, Y. et al., "Newly designed polysiloxane-graft-poly (oxyethylene) copolymeric surfactants: preparation, surface activity and emulsification properties," Colloid & Polymer Science 272, pp. 684-691, (1994).

Shah, Rhutesh K. et al., "Polymers fit for function Making emulsions drop by drop," Materials Today, vol. 11, No. 4, pp. 18-27, Apr. 2008.

Shendure, Jay et al., "Next-generation DNA sequencing," Nature Biotechnology, vol. 26, No. 10, pp. 1135-1145, Oct. 2008.

Shuber, Anthony P. et al., "A Simplified Procedure for Developing Multiplex PCRs," Genome Research, published by Cold Spring Harbor Laboratory Press, pp. 488-493, (1995).

Shuming Nie et al., "Optical Detection of Single Molecules," Annu. Rev. Biophys. BiomoL Struct. vol. 26, pp. 567-596, (1997).

Sigma-Aldrich, "Synthesis of Mesoporous Materials," Material Matters, 3.1, 17, (2008).

Singley, Edith J. et al., "Phase behavior and emulsion formation of novel fluoroether amphiphiles in carbon dioxide," Fluid Phase Equilibria 128, pp. 199-219, (1997).

O'Lenick, Jr., Anthony J., "Silicone Emulsions and Surfactants," Journal of Surfactants and Detergents, vol. 3, No. 3, Jul. 2000.

Pamme, Nicole, "continuous flow separations in microfluidic devices," Lab on a Chip, vol. 7, pp. 1644-1659, Nov. 2, 2007.

Piatyszek, Mieczyslaw A. et al., "Detection of telomerase activity in human cells and tumors by a telomeric repeat amplification protocol (TRAP)," Methods in Cell Science 17, pp. 1-15, (1995).

Pinheiro, Leonardo B. et al., "Evaluation of a Droplet Digital Polymerase Chain Reaction Format for DNA Copy Number Quantification", Analytical Chemistry, vol. 84, Jan. 17, 2012, pp. 1003-1011.

Pohl, Gudrun et al., "Principle and applications of digital PCR" review, www.future-drugs.com, Expert Rev. Mol. Diagn. 4(1), pp. 41-47, (2004).

Polydimethylsiloxane, 5 pgs., published in FNP 52 (1992).

Price, Christopher B., "Regular Review Point of Care Testing," BMJ, vol. 322, May 26, 2001.

Qin, Jian et al., "Studying copy number variations using a nanofluidic platform," Nucleic Acids Research, vol. 36, No. 18, pp. 1-8, Aug. 18, 2008.

Roach, L. Spencer et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.

Rutledge, R. G. et al., "Mathematics of quantitative kinetic PCR and the application of standard curves," Nucleic Acids Research, vol. 31, No. 16, pp. 1-6, (2003).

Rutledge, R. G., "Sigmoidal curve-fitting redefines quantitative real-time PCR with the prospective of developing automated high-throughput applications," Nucleic Acids Research. vol. 32, No. 22, pp. 1-8, (2004).

Wang, Anfeng et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Weaver, Suzanne et al., "Taking qPCR to a higher level: Analysis of CNV reveals the power of high throughput qPCR to enhance quantitative resolution," Methods, vol. 50, pp. 271-276, Jan. 15, 2010.

Weitz, David A., "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.

(56) References Cited

OTHER PUBLICATIONS

Wetmur, James G. et al., "Linking Emulsion PCR Haplotype Analysis," PCR Protocols, Methods in Molecular Biology, vol. 687, pp. 165-175, (2011).
Wetmur, James G. et al., "Molecular haplotyping by linking emulsion PCR: analysis of paraoxonase 1 haplotypes and phenotypes," Nucleic Acids Research, vol. 33, No. 8, pp. 2615-2619, (2005).
Williams, Richard et al., "Amplification of complex gene libraries by emulsion PCR," Nature Methods, vol. 3, No. 7, pp. 545-550, Jul. 2006.
Yazdi, A. V. et al., "Highly Carbon Dioxide Soluble Surfactants, Dispersants and Chelating Agents," Fluid Phase Equilibria, vol. 117, pp. 297-303, (1996).
Young, Lee W., Authorized officer, International Searching Authority, International Search Report, PCT Application No. PCT/US 201046519; dated Oct. 15, 2010.
Young, Lee W., Authorized officer, International Searching Authority, Written Opinion of the International Searching Authority, PCT Application No. PCT/US 201046519; dated Oct. 15, 2010.
Zhang, Chunsun et al., "Miniaturized PCR chips for nucleic acid amplification and analysis: latest advances and future trends," Nucleic Acids Research, vol. 35, No. 13, pp. 4223-4237, Jun. 18, 2007.
Smid-Korbar, J. et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.
Snow, Steven A., "Synthesis and Characterization of Zwitterionic Silicone Sulfobetaine Surfactants," Langmuir, vol. 6, No. 2, American Chemical Society, pp. 385-391, (1990).
Solimini, Nicole L. et al., "Recurrent Hemizygous Deletions in Cancers May Optimize Proliferative Potential," Science, vol. 337, pp. 104-109, Jul. 6, 2012.
Swillens, Stéphane et al., "Instant evaluation of the absolute initial number of cDNA copies from a single real-time PCR curve," Nucleic Acids Research, vol. 32, No. 6, pp. 1-6, (2004).

Tanner, Nathan A. et al., "Simultaneous multiple target detection in real-time loop-mediated isothermal amplification," BioTechniques, vol. 53, pp. 8-19, Aug. 2012.
Teh, Shia-Yen et al., "Droplet microfluidics", Lab on a Chip, vol. 8, Jan. 11, 2008, pp. 198-220.
Thinxxs Microtechnology AG, "Emerald Biosystems: Protein Crystallization," 1 pg., downloaded Mar. 8, 2011.
Thurecht, Kristofer J. et al., "Investigation of spontaneous microemulsion formation in supercritical carbon dioxide using high-pressure NMR," Journal of Supercritical Fluids, vol. 38, pp. 111-118, (2006).
Thurecht, Kristofer J. et al., "Kinetics of Enzymatic Ring-Opening Polymerization of ∈-Caprolactone in Supercritical Carbon Dioxide," Macromolecules, vol. 39, pp. 7967-7972, (2006).
Vogelstein, Bert et al., "Digital PCR," Proc. Natl. Acad. Sci. USA, vol. 96, pp. 9236-9241, Aug. 1999.
Vulto, Paul et al., "Phaseguides: a paradigm shift in microfluidic priming and emptying," Lab on a Chip, vol. 11, No. 9, pp. 1561-1700, May 7, 2011.
Zhang, Tianhao et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
Zhao, Yuejun et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Zhelev, Toshko et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).
Zhong, Qun et al., "Multiplex digital PCR: breaking the one target per color barrier of quantitative PCR," Lab on a Chip, vol. 11, pp. 2167-2174, (2011).
Zimmermann, Bernhard G. et al., "Digital PCR: a powerful new tool for noninvasive prenatal diagnosis?," Prenatal Diagnosis, vol. 28 pp. 1087-1093, Nov. 10, 2008.

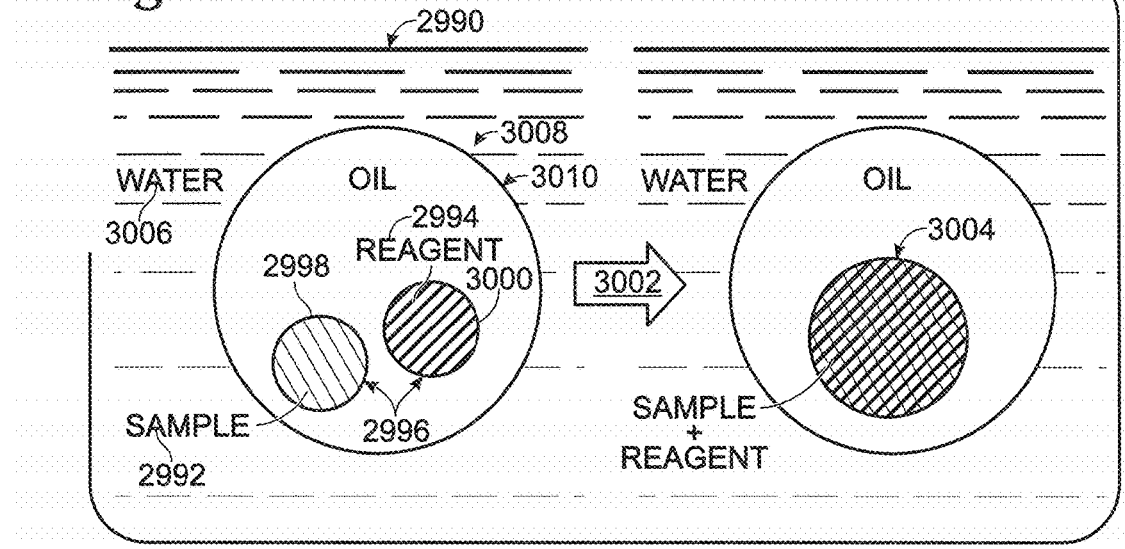
Fig. 8
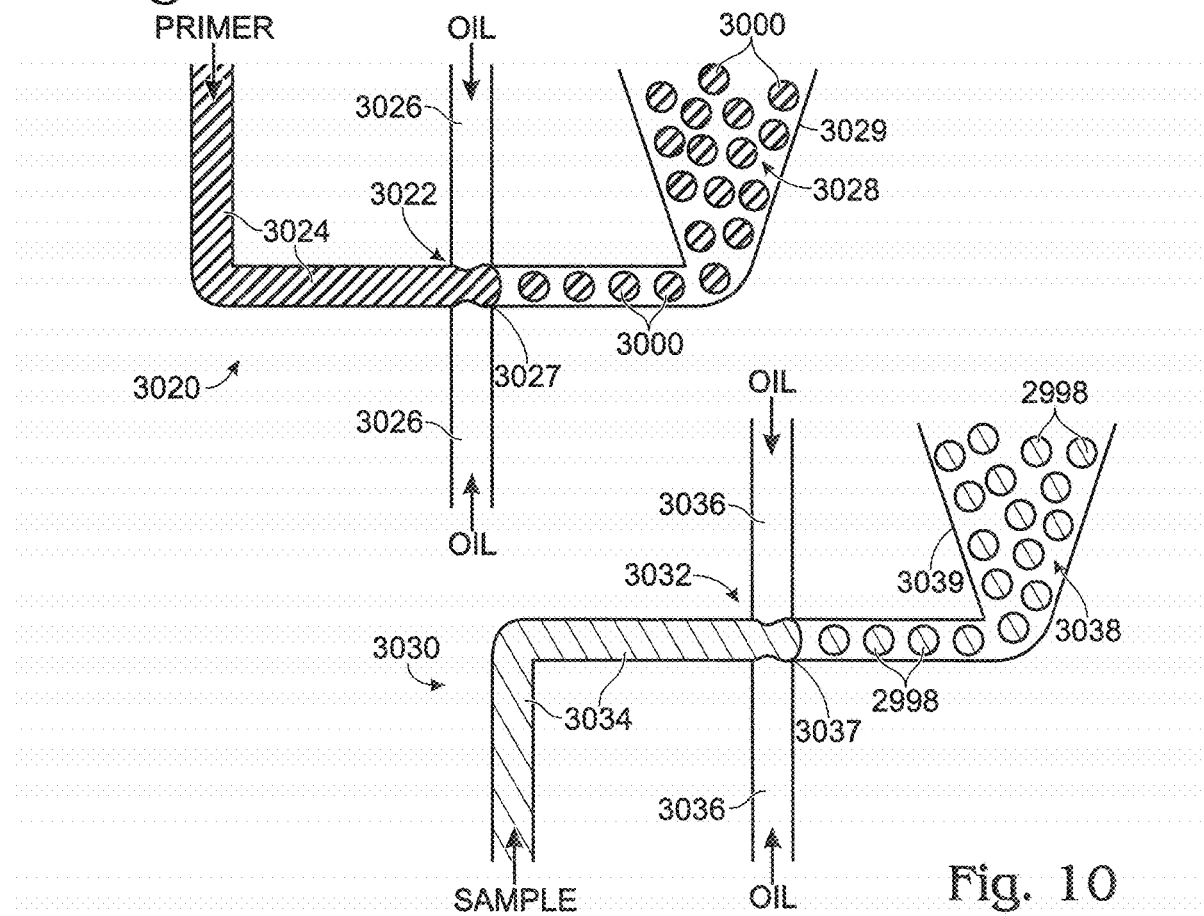
Fig. 9
Fig. 10

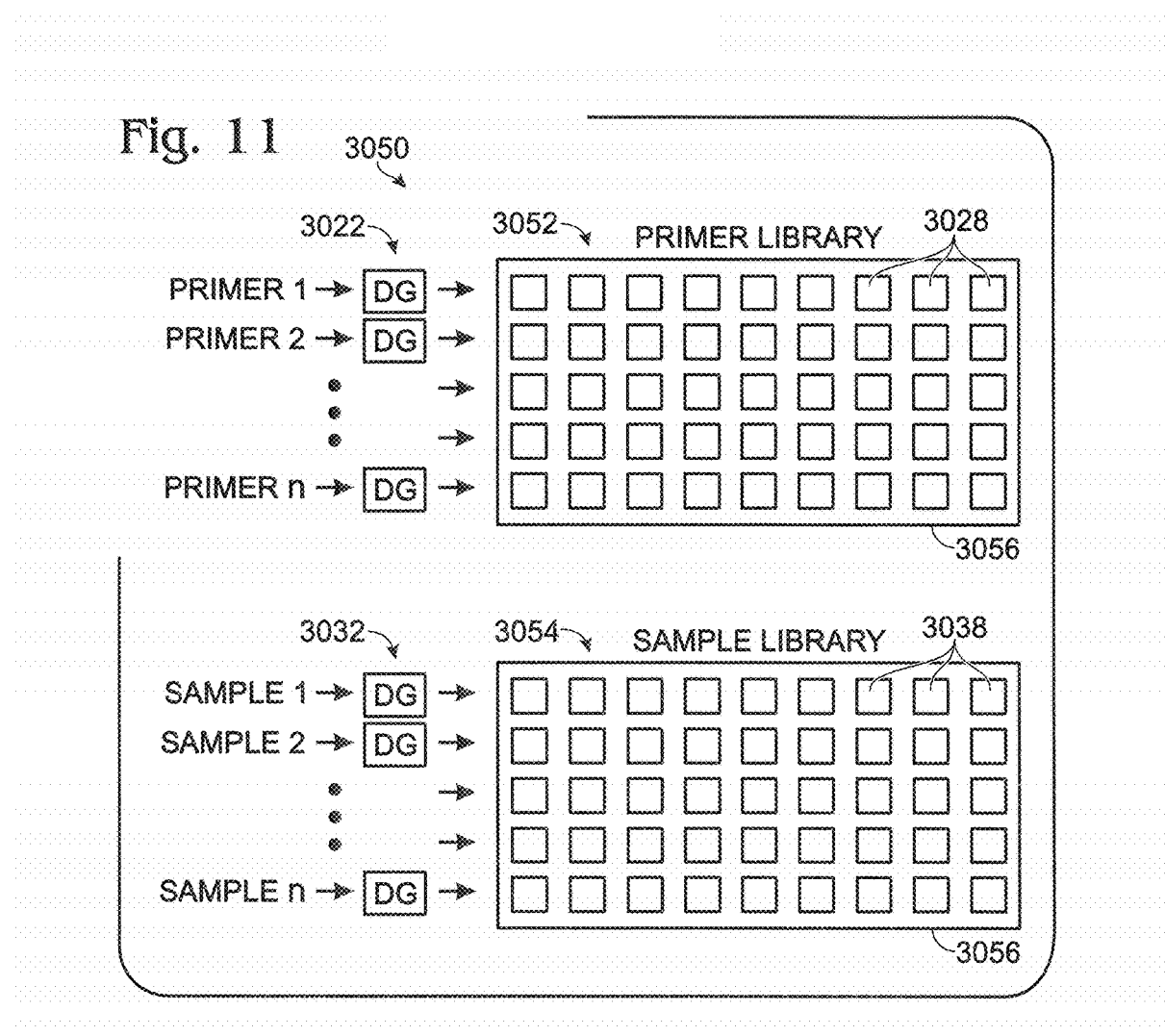

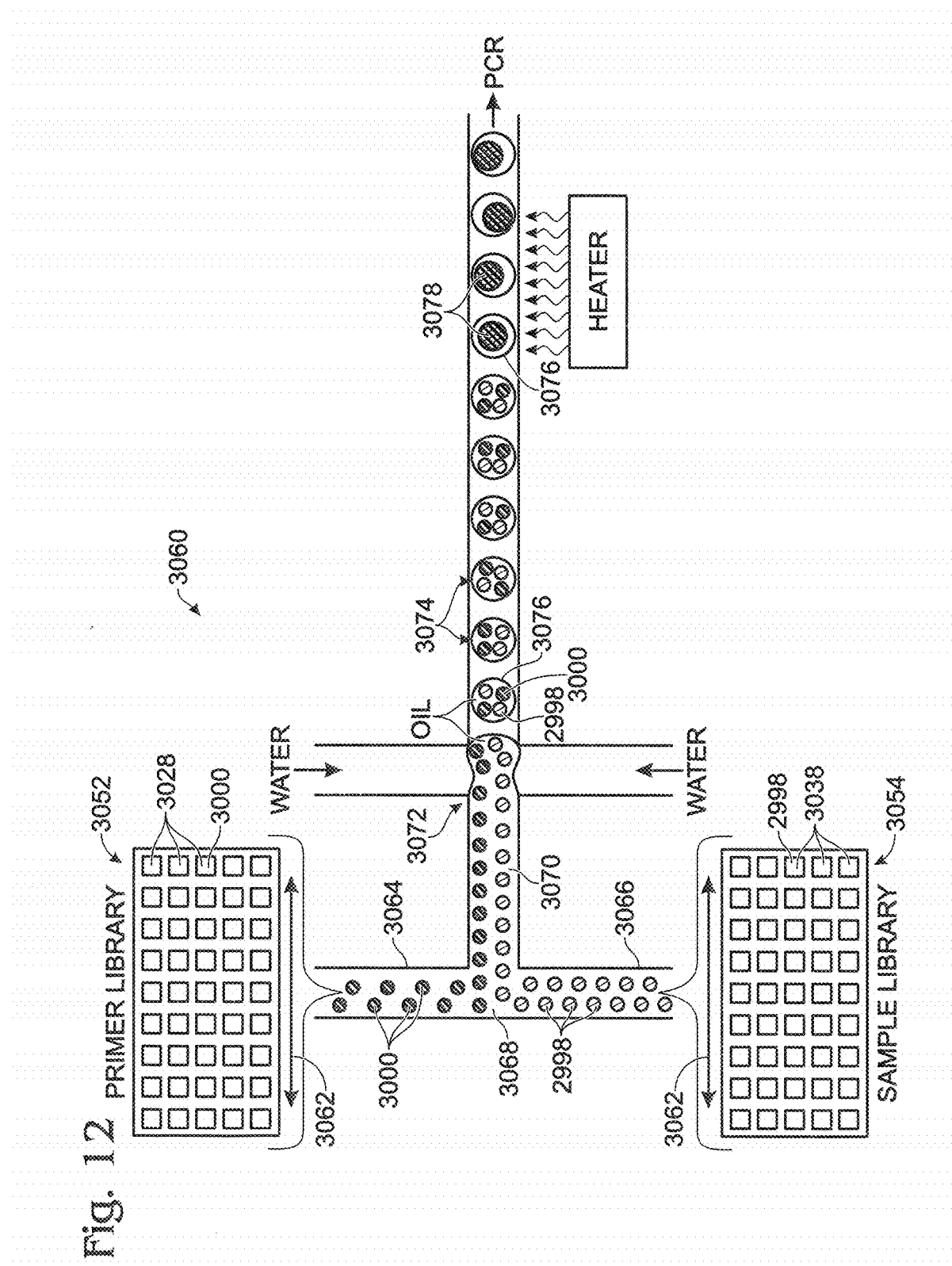

SYSTEM FOR MIXING FLUIDS BY COALESCENCE OF MULTIPLE EMULSIONS

CROSS-REFERENCES TO PRIORITY APPLICATIONS

This application is a continuation of U.S. patent application Ser. No. 12/862,542, filed Aug. 24, 2010, now U.S. Pat. No. 9,194,861, which, in turn, is based upon and claims the benefit under 35 U.S.C. § 119(e) of U.S. Provisional Patent Application Ser. No. 61/275,860, filed Sep. 2, 2009. Each of these priority patent applications is incorporated herein by reference in its entirety for all purposes.

CROSS-REFERENCES TO ADDITIONAL MATERIALS

This application incorporates by reference in their entireties for all purposes the following materials: U.S. Pat. No. 7,041,481, issued May 9, 2006; U.S. Patent Application Publication No. US-2010-0173394-A1, published Jul. 8, 2010; and Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples combined with reagents. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

The trend is toward reduced volumes and detection of more targets. However, mixing smaller volumes can require more complex instrumentation, which increases cost. Accordingly, improved technology is needed to permit testing more combinations of samples and reagents, at a higher speed, a lower cost, and/or with reduced instrument complexity.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (picoliters to nanoliters) can be utilized, allowing earlier detection by increasing reaction rates and forming more concentrated products. Also, a much greater number of independent measurements (thousands to millions) can be made on the sample, when compared to conventional bulk volume reactions performed on a micoliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nuclei acid target molecules in droplets using the polymerase chain reaction (PCR).

Compartmentalization of single molecules of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

Despite their allure, emulsion-based assays present technical challenges for high-throughput testing, which can require tens, hundreds, thousands, or even millions of individual sample/reagent combinations. Samples and reagents for emulsion-based assays generally can be mixed more easily and reliably in relatively large volumes (e.g., microliters) before formation of emulsions, but this approach consumes substantial quantities of sample and reagent. In contrast, controlled mixing of picoliter to nanoliter volumes of samples with reagents conserves sample and reagent. However, mixing of these small volumes in emulsions can require complex instrumentation that is difficult to scale-up for performing high-throughput, emulsion-based assays with many different samples and/or reagents. For example, emulsions of sample droplets and of reagent droplets can be formed separately, and then individual droplets of sample and reagent can brought into proximity and merged using electro-coalescence. Nevertheless, this technique generally requires precise timing of trains of sample droplets and reagent droplets, active feedback loops, and smooth flow, thereby increasing complexity and cost.

There remains a need for methods and apparatus to accomplish mixing of sub-microliter volumes of samples and reagents, such as mixing of selected samples and reagents on-demand.

SUMMARY

The present disclosure provides a system, including methods, apparatus, compositions, and kits, for the mixing of small volumes of fluid by coalescence of multiple emulsions.

BRIEF DESCRIPTION OF THE DRAWINGS

FIG. 8 is a diagram illustrating exemplary coalescence of another multiple emulsion to achieve mixing of small volumes of a sample and a reagent within a compound droplet by fusion of inner droplets, namely, at least one sample droplet and at least one reagent droplet, in accordance with aspects of the present disclosure.

FIG. 9 is a schematic view of an exemplary device for forming a precursor emulsion of reagent droplets (e.g., primer droplets), which can be modified to create the multiple emulsion of FIG. 8, in accordance with aspects of the present disclosure.

FIG. 10 is a schematic view of an exemplary device for forming a precursor emulsion of sample droplets, which can be combined with the reagent droplets of FIG. 8 in a multiple emulsion, in accordance with aspects of the present disclosure.

FIG. 11 is a schematic view of an exemplary system for forming a library of reagent droplets and a library of sample droplets, with members of each library disposed in an array that can be accessed dynamically, in accordance with aspects of the present disclosure.

FIG. 12 is a schematic view of a yet another exemplary device for creating and coalescing multiple emulsions, with the device in the process of (a) transforming a mixture of a sample emulsion and a primer emulsion into a multiple emulsion and (b) fusing sample and primer droplets within individual compound droplets of the multiple emulsion, in accordance with aspects of present disclosure.

DETAILED DESCRIPTION

Figure 1:
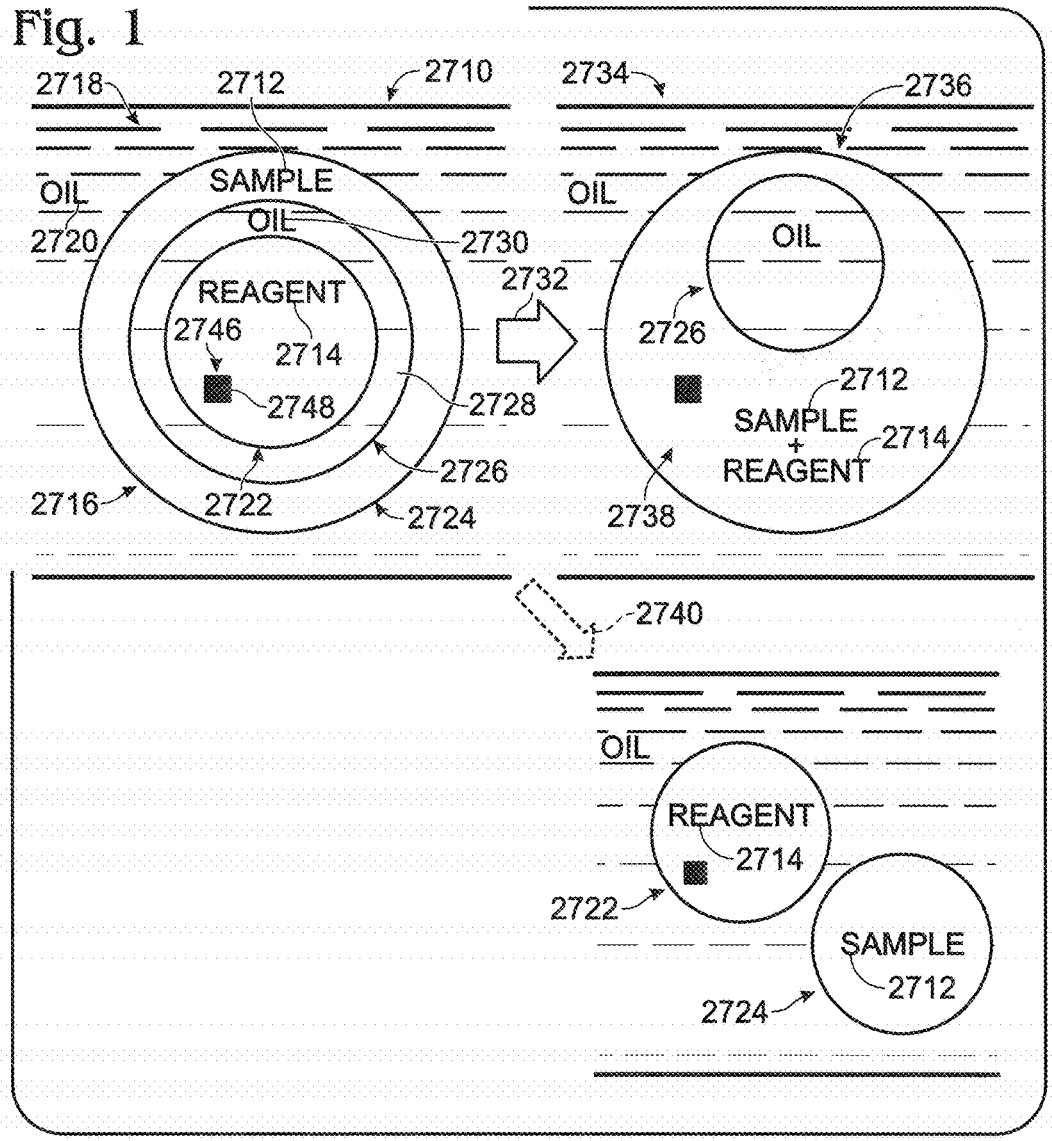
FIG. 1 is a diagram illustrating exemplary coalescence of inner and outer droplets within a compound droplet of a multiple emulsion to achieve mixing of small volumes of sample and reagent within compound droplets, in accordance with aspects of the present disclosure.

The present disclosure provides a system, including methods, apparatus, compositions, and kits, for mixing small volumes of fluid by coalescence of multiple emulsions. The multiple emulsions may be configured to be inducibly coalesced, such as by heating, to provide controlled mixing of small volumes of fluid.

A multiple emulsion, also termed a compound emulsion and/or droplets within droplets, generally comprises compound droplets dispersed in an immiscible carrier fluid (e.g., oil or water) that forms a continuous phase. Each compound droplet may include at least one sample droplet (i.e., at least one sample-containing droplet) and at least one reagent droplet (i.e., at least one reagent-containing droplet). The at least one sample droplet and the at least one reagent droplet of a compound droplet may be inner droplets or may be at least one inner droplet disposed within an outer droplet (or vice versa). In any event, the sample and reagent droplets may be miscible with one another (e.g., both being aqueous), but may be separated from one another by at least one layer of immiscible fluid (e.g., an oil), which may have the same composition as, or a distinct composition from, the continuous phase. The layer of immiscible fluid may be provided by a barrier droplet. The barrier droplet may be an outer droplet that encapsulates both the sample droplet and the reagent droplet (if both the sample and reagents droplets are inner droplets) or an intermediate droplet that encapsulates the sample droplet or the reagent droplet, but not both (if the sample and reagent droplets are inner and outer droplets (or vice versa)). In any event, immiscible fluid may serve as a barrier that keeps the sample and reagent droplets of each compound droplet isolated from one another, such as until mixing is desired. In some embodiments, the multiple emulsion may be a water-in-oil-in-water-in-oil (W/OW/O) emulsion or a water-in-oil-in-water (W/O/W) emulsion, when described according to the fluid predominant in each phase.

The sample and reagent droplets of a compound droplet, collectively, may provide an assay mixture for performing a test of interest on a partition of the sample. For example, the sample droplet may include a partition of a sample to be tested and the reagent droplet (or two or more types of reagent droplets within a compound droplet) may include at least one reagent for the test. Prior to coalescence, the sample and the reagent droplets may be isolated from one another by the barrier droplet. In some embodiments, the sample droplet and the reagent droplet, collectively, may provide a complete assay composition that includes a partition of a sample and all of the chemical components necessary to perform a particular test on the sample partition.

The sample and reagent droplets of individual compound droplets may be fused (coalesced) to cause mixing of the contents of the sample and reagent droplets. Mixing may, for example, start a reaction, stop a reaction, and/or permit a reaction to occur, among others. Fusion may occur spontaneously and/or may be induced to initiate mixing at a desired time. If fusion is inducible, fusion may be induced controllably and/or selectively by any suitable treatment, such as changing (e.g., elevating) the temperature of the multiple emulsion. At a first temperature or in a first temperature range, such as a lower temperature or temperature range (e.g., from about 0° C. to 40° C.), the sample and reagent droplets may remain isolated from one another. Also, at a second temperature or in a second temperature range, such as an elevated (higher) temperature or range (e.g., above about 40° C.), fusion of the sample and reagent droplets within compound droplets may be induced. Thus, fusion may be induced by heating (or cooling) the multiple emulsion.

The multiple emulsions disclosed herein may have any other suitable features. Each size of droplet within a multiple emulsion (e.g., inner droplets, outer droplets, intermediate droplets, and/or barrier droplets, among others) may be sized uniformly, for example, with a standard deviation of the diameter that is less than about 20%, 10%, or 5% of the mean diameter for that size of droplet. Alternatively, or in addition, any of the compound droplets disclosed herein may be labeled with a predefined code. Code labeling may permit analysis of a mixture of distinct types of compound droplets and/or fused droplets, by using corresponding, distinguishable codes to identify the distinct types. The distinct types of compound droplets/fused droplets may contain distinct samples, distinct reagents, or both, with each distinct sample and/or reagent being identifiable through its associated, distinguishable code. Accordingly, the multiple emulsion may permit assay of a plurality of samples with the same reagent (i.e., performing the same test on different samples), assay of a sample with a plurality of different reagents (i.e., performing different tests on the same sample), or assay of a plurality of samples with a plurality of reagents (i.e., performing a plurality of tests on each of a plurality of samples).

The multiple emulsion may include at least one surfactant, or two or more different surfactants, which may stabilize the multiple emulsion. The concentration of each surfactant may be selected to stabilize the multiple emulsion for preparation and storage, while enabling destabilization of particular types of droplets of the multiple emulsion when coalescence is induced, such as at an elevated temperature. In some examples, a hydrophilic surfactant may be present in at least one aqueous phase and a hydrophobic surfactant in at least one immiscible phase (e.g., an oil phase) of the multiple emulsion, in corresponding fluid streams used to form any these phases of the multiple emulsion, and/or in corresponding phases of a fused emulsion produced from the multiple emulsion.

The present disclosure also provides methods for testing samples. A multiple emulsion may be obtained. The multiple emulsion may include a plurality of compound droplets containing one or more samples and disposed in an immiscible continuous phase. Each compound droplet may include an inner droplet and an outer droplet separated by a layer of immiscible fluid. The inner droplet and the outer droplet of individual compound droplets may be fused to form fused droplets that mix partitions of a sample with a reagent. The sample may be provided by the inner droplet and the reagent by the outer droplet, or vice versa. Fusion may occur, optionally, with induction, such as by elevating a temperature of the compound droplets. Signals may be detected from the fused droplets, with the signals representing a result of a test performed on the partitions of the sample with the reagent in the fused droplets.

The systems disclosed herein may offer substantial advantages over other approaches to mixing small volumes of fluid. These advantages may include any combination of the following: (1) an ability to mix small volumes of reactants with a sample on-demand; (2) scalable methods and apparatus to accomplish mixing of a large number of reagents with a sample in small-volume reaction vessels (e.g., femtoliter, picoliter, or nanoliter), a large numbers of samples with a reagent in small-volume reaction vessels, and/or reagents with samples in small volumes using reproducible processes on low-cost instrumentation; (3) high-throughput fluid mixing that uses minimum amounts of reagents to reduce assay costs; (4) an ability to screen a sample for the presence of one or up to thousands or more targets on the same instrument; (5) an activation step that can initiate mixing of small volumes and that does not require complex timing of droplet streams using precision instrumentation; (6) an ability to perform more complex mixing steps at a centralized facility, to permit an end user's instrument to have less complexity, thereby making tests easier to perform; (7) a high-throughput assay platform that reduces the number of consumables per test; and/or (8) accommodation of many test reagents and samples with a simplified instrument architecture with minimized fluidic complexity (such as by reducing the number of fluidic connections, valves, etc.).

Further aspects of the present disclosure are presented in the following sections: (I) definitions, (II) coalescence of a multiple emulsion, (III) system overview, (IV) formation and mixing of precursor emulsions, (V) formation and coalescence of a mixed emulsion, and (VI) multiple emulsions providing fusion of inner droplets with one another.

I. DEFINITIONS

Technical terms used in this disclosure have the meanings that are commonly recognized by those skilled in the art. However, the following terms may have additional meanings, as described below.

Emulsion—a composition comprising liquid droplets disposed in an immiscible liquid. The droplets are formed by at least one dispersed phase, and the immiscible liquid forms a continuous phase. The continuous phase can also or alternatively be termed a carrier and/or a carrier phase. The dispersed phase (or at least one of the dispersed phases of a multiple emulsion) is immiscible with the continuous phase, which means that the dispersed phase (i.e., the droplets) and the continuous phase (i.e., the immiscible liquid) do not mix to attain homogeneity. The droplets can have any uniform or nonuniform distribution in the continuous phase. The droplets are isolated from one another by the continuous phase and encapsulated (i.e., enclosed/surrounded) by the continuous phase. An emulsion may be monodisperse, that is, composed of droplets of uniform size, or may be polydisperse, that is, composed of droplets of various sizes. If monodisperse, the droplets of the emulsion may vary in size by a standard deviation of the volume (or diameter) that is less than about 50%, 20%, 10%, or 5% of the average droplet volume (or diameter).

An emulsion may have any suitable composition. The emulsion may be characterized by the predominant liquid compound or type of liquid compound in each phase. The predominant liquid compounds in the emulsion may be water and oil. For example, the emulsion may be a water-in-oil (W/O) emulsion (i.e., a dispersed aqueous phase in a continuous oil phase), an oil-in-water (O/W) emulsion, an oil-in-water-in-oil (O/W/O) emulsion, a water-in-oil-in-water-in-oil (W/O/W/O) emulsion, or the like. Any other suitable components may be present in any of the emulsion phases, such as at least one surfactant, reagent, sample, other additive, label, or any combination thereof.

"Oil" may be any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others.

Partition—a separated portion of a bulk volume. The partition may be a sample partition (or a reagent partition) generated from a sample (or a reagent) included in the bulk volume. Partitions generated from a bulk volume may be substantially uniform in size or may have distinct sizes (e.g., sets of partitions of two or more discrete, uniform sizes). Partitions may be liquid partitions, which are partitions that have a liquid periphery and/or are at least predominantly, by volume, a liquid phase. Exemplary liquid partitions are droplets or slugs.

Droplet—a small volume of a first liquid that is encapsulated by an immiscible second liquid, such as a continuous phase of an emulsion (and/or by a larger droplet). The volume of a droplet, and/or the average volume of droplets in an emulsion, may, for example, be less than about one microliter (or between about one microliter and one nanoliter or between about one microliter and one picoliter), less than about one nanoliter (or between about one nanoliter and one picoliter), or less than about one picoliter (or between about one picoliter and one femtoliter), among others. A droplet (or droplets of an emulsion) may have a diameter (or an average diameter) of less than about 1000, 100, or 10 micrometers, or about 1000 to 10 micrometers, among others. A droplet may be spherical or nonspherical. A droplet may be a simple droplet or a compound droplet.

Compound droplet—a droplet in which at least one droplet encapsulates at least one other droplet. A compound droplet includes at least two immiscible liquids, with one of the liquids encapsulating the other liquid in the compound droplet to form at least one droplet within a droplet. A droplet that is encapsulated by another droplet may be described as an inner droplet, which may or may not be the innermost droplet of a compound droplet. A droplet encapsulating another droplet may be described as an outer droplet, which may or may not be the outermost droplet of a compound droplet. In contrast to a compound droplet, a simple droplet is not encapsulated by another droplet.

Multiple emulsion—an emulsion including compound droplets. A multiple emulsion can be characterized according to the level of encapsulation of its constituent compound droplets, with a higher-order emulsion having more levels of encapsulation than a lower-order emulsion. For example, a double emulsion contains compound droplets structured as a droplet within a droplet, a triple emulsion contains compound droplets structured as a droplet within a droplet within a droplet, and so on. In contrast, a single emulsion contains simple droplets in a continuous phase.

Precursor emulsion—an emulsion that provides pre-existing droplets for further encapsulation. A precursor emulsion may be a single emulsion, which may be processed by further encapsulation to form a multiple emulsion, or may be a lower-order multiple emulsion, which may be processed by further encapsulation to form a higher-order multiple emulsion.

Surfactant—a surface-active substance capable of reducing the surface tension of a liquid in which it is dissolved. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. A hydrophilic surfactant may have a greater affinity for water than oil, while a hydrophobic surfactant may have a greater affinity for oil than water. The emulsions disclosed herein and/or any phase thereof, may include at least one hydrophilic surfactant, at least one hydrophobic surfactant, or a combination thereof. Alternatively, or in addition, the emulsions disclosed herein and/or any phase thereof, may include at least one nonionic (and/or ionic) detergent. Furthermore, an emulsion disclosed herein and/or any phase thereof may include a surfactant comprising polyethyleneglycol, polypropyleneglycol, or Tween 20, among others.

Test—a procedure(s) and/or reaction(s) used to characterize something, and any signal(s), value(s), data, and/or result(s) obtained from the procedure(s) and/or reaction(s). A test also may be described as an assay. A test may be performed using at least one "test mixture" or "assay mixture," which is a composition from which one or more test signals are detected, before, during, and/or after processing of the composition to permit a reaction, if any, to occur. A test or assay may determine a presence (e.g., concentration) or activity, among others, of one or more analytes in a sample.

Reaction—a chemical reaction, a binding interaction, a phenotypic change, or a combination thereof. An exemplary reaction is enzyme-catalyzed conversion of a substrate to a product and/or binding of a substrate or product to a binding partner.

Sample—a compound, composition, and/or mixture of interest, from any suitable source(s). A sample is the general subject of interest for a test that analyzes an aspect of the sample, such as an aspect related to at least one analyte that may be present in the sample. Samples may be analyzed in their natural state, as collected, and/or in an altered state, for example, following storage, preservation, extraction, lysis, dilution, concentration, purification, filtration, mixing with one or more reagents, partitioning, further processing, or any combination thereof, among others. Clinical samples may include blood, saliva, urine, stool, sputum, mucous, milk, a fluid aspirate, and/or tissue, among others. Environmental samples may include water, soil, and/or air, among others. Research samples may include cultured cells, primary cells, viruses, small organisms, or the like. Additional samples may include foodstuffs, weapons components, suspected contaminants, and so on.

Analyte—a component(s) or potential component(s) of a sample that is analyzed in a test. An analyte is a specific subject of interest in a test for which the sample is the general subject of interest. An analyte may, for example, be a nucleic acid, a protein, an enzyme, a cell, a virus, an organelle, a macromolecular assembly, a drug candidate (and/or potential drug), a lipid, a carbohydrate, an inorganic substance, or any combination thereof, among others. An analyte may be tested for its presence, activity, and/or other characteristic in a sample. The presence of an analyte may relate to an absolute or relative number, concentration, binary assessment (e.g., present or absent), or the like, of the analyte in a sample or in one or more partitions thereof.

Reagent—a compound, set of compounds, and/or composition that is combined with a sample in order to perform a particular test on the sample. A reagent may be a target-specific reagent, which is any reagent composition that confers specificity for detection of a particular target or analyte in a test. A reagent optionally may include a chemical reactant and/or a binding partner for the test. A reagent may, for example, include at least one nucleic acid, protein (e.g., an enzyme), cell, virus, organelle, macromolecular assembly, a potential drug, a lipid, a carbohydrate, an inorganic substance, or any combination thereof, among others. In exemplary embodiments, the reagent may be an amplification reagent, such as at least one primer or a pair of primers for amplification of a target, and/or at least one probe to provide an amplification signal.

Nucleic acid—a compound comprising a chain of nucleotide monomers. A nucleic acid may be single-stranded or double-stranded (i.e., base-paired with another nucleic acid), among others. The chain of a nucleic acid may be composed of any suitable number of monomers, such as at least about ten or one hundred, among others. Generally, the length of a nucleic acid chain corresponds to its source, with synthetic nucleic acids (e.g., nucleic acid reagents such as primers and probes) typically being shorter and biologically produced nucleic acids (e.g., nucleic acid analytes) typically being longer.

A nucleic acid can have a natural or artificial structure, or a combination thereof. Nucleic acids with a natural structure, namely, deoxyribonucleic acid (DNA) and ribonucleic acid (RNA), have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid is defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of adenine-thymine and guanine-cytosine base pairs with the other nucleic acid is termed "complementary."

Replication—a process forming a complementary copy of a nucleic acid or a segment thereof. The nucleic acid and/or segment replicated is a template (and/or a target) for replication.

Amplification—a process in which a copy number increases. Amplification may be a process in which replication occurs repeatedly over time to form multiple copies of a template. Amplification can produce an exponential or linear increase in the number of copies as amplification proceeds. Exemplary amplification strategies include polymerase chain reaction (PCR), loop-mediated isothermal amplification (LAMP), rolling circle replication (RCA), cascade-RCA, nucleic acid based amplification (NASBA), and the like. Also, amplification can utilize a linear or circular template. Amplification can be performed under any suitable temperature conditions, such as with thermal cycling or isothermally. Furthermore, amplification can be performed, or tested for its occurrence, in an amplification mixture, which is any composition capable of amplifying a nucleic acid target, if any, in the mixture. An amplification mixture can include any combination of at least one primer, at least one probe, at least one replication enzyme (e.g., at least one polymerase, such as at least one DNA and/or RNA polymerase), deoxynucleotide (and/or nucleotide) triphosphates (dNTPs and/or NTPs), or any combination thereof, among others.

PCR—amplification that relies on repeated cycles of heating and cooling (i.e., thermal cycling) to achieve successive rounds of replication. PCR can be performed by thermal cycling between two or more temperature setpoints, such as a higher denaturation temperature and a lower annealing/extension temperature, or among three or more temperature setpoints, such as a higher denaturation temperature, a lower annealing temperature, and an intermediate extension temperature, among others. PCR can be performed with a thermostable polymerase, such as Taq DNA polymerase. PCR generally produces an exponential increase in the amount of a product amplicon over successive cycles.

RT-PCR (reverse transcription-PCR)—PCR utilizing a complementary DNA template produced by reverse transcription of RNA. RT-PCR permits analysis of an RNA sample by (1) forming complementary DNA copies of RNA, such as with a reverse transcriptase enzyme, and (2) PCR amplification using the complementary DNA as a template.

Real-time PCR—a PCR-based analysis in which amplicon formation is measured during the reaction, such as after completion of each thermal cycle. Real-time PCR generally provides quantification of a target based on the kinetics of target amplification.

Endpoint PCR—a PCR-based analysis in which amplicon formation is measured after completion of thermal cycling. Endpoint PCR generally provides a qualitative (yes/no) determination of whether a nucleic acid target is present (at a detectable level) in an amplification mixture.

Amplicon—a product of an amplification reaction. An amplicon can be single-stranded or double-stranded, or a combination thereof. An amplicon corresponds to any suitable segment or the entire length of a nucleic acid target.

Primer—a nucleic acid capable of, and/or used for, priming replication of a nucleic acid template. Thus, a primer is a shorter nucleic acid that is complementary to a longer template. During replication, the primer is extended, based on the template sequence, to produce a longer nucleic acid that is a complimentary copy of the template. A primer may be DNA, RNA, or an analog thereof (i.e., an artificial nucleic acid), and may have any suitable length, such as at least about 10, 15, or 20 nucleotides. Exemplary primers are synthesized chemically. Primers may be supplied as a pair of primers for amplification of a nucleic acid target. The pair of primers may be a sense primer and an antisense primer that collectively define the opposing ends (and thus the size) of a resulting amplicon.

Probe—a nucleic acid connected to a label. A probe may be a sequence-specific binding partner for a nucleic acid target and/or amplicon. An exemplary probe includes one or more nucleic acids connected to a pair of dyes that collectively exhibit fluorescence resonance energy transfer (FRET) when proximate one another. The pair of dyes may respectively provide first and second emitters or an emitter (a reporter) and a quencher. Fluorescence emission from the pair of dyes changes when the dyes are separated from one another, such as by cleavage of the probe (e.g., a Taqman probe) during primer extension, or when the probe (e.g., a molecular beacon probe) binds to an amplicon.

Label—an identifying and/or distinguishing marker or identifier connected to or incorporated into any entity, such as a molecule, molecular complex, compound, biological particle, or droplet. The label may be described as labeling the particular entity to produce a labeled entity. A label may, for example, be a dye that renders an entity optically detectable or at least more optically detectable. Exemplary dyes used for labeling are fluorescent dyes (fluorophores) and fluorescence quenchers.

Code—a mechanism for differentiating one type of droplet (e.g., containing a first sample and/or reagent) from one or more other types of droplet (e.g., containing a second sample and/or reagent) in a mixture of the droplet types. A code also or alternatively may be described as a barcode or an identifier. Exemplary codes to differentiate different types of droplets may include different droplet sizes, dyes, combinations of dyes, amounts of one or more dyes, enclosed code particles, or any combination thereof, among others.

Binding partner—a member of a pair of members that bind to one another. Each member may be an atom, molecule, molecular complex, compound, and/or biological particle (a cell, virus, organelle, or the like), among others. Binding partners may bind specifically to one another. Specific binding can be characterized by a dissociation constant of less than about $10^{-4}$, $10^{-6}$, $10^{-8}$, or $10^{-10}$ M.

Exemplary specific binding partners include biotin and avidin/streptavidin, a sense nucleic acid and a complementary antisense nucleic acid, a primer and its target, an antibody and a corresponding antigen, a receptor and its ligand, a nucleic acid and a protein that recognizes a sequence motif present in the nucleic acid, and the like.

Channel—an elongate passage for fluid travel. A channel generally includes at least one inlet, where fluid enters the channel, and at least one outlet, where fluid exits the channel. The functions of the inlet and the outlet may be interchangeable, that is, fluid may flow through a channel in only one direction or in opposing directions, generally at different times. A channel may include walls that define and enclose the passage between the inlet and the outlet. A channel may be formed by a tube (i.e., a hollow, at least generally cylindrical structure) and/or in or on a planar structure (e.g., a chip), among others. A channel may or may not branch. A channel may be linear or nonlinear. Exemplary nonlinear channels include a channel extending along a planar flow path or a nonplanar flow path (e.g., a helical flow path). A channel may be a microfluidic channel, which is a channel having a characteristic transverse dimension (e.g., the channel's average diameter) of less than about one millimeter.

II. COALESCENCE OF A MULTIPLE EMULSION

FIG. 1 shows a process of coalescing an exemplary multiple emulsion 2710 to achieve mixing of small volumes of fluid, such as small volumes of fluid containing a sample 2712 and a reagent 2714.

Multiple emulsion 2710 may include a plurality of compound droplets 2716 disposed in a continuous carrier phase 2718, namely, an immiscible fluid or liquid, such as an oil 2720. (Only one compound droplet 2716 of the multiple emulsion is shown here to simplify the presentation.) Each compound droplet 2716 may include at least one reagent droplet containing one or more reagents and at least one sample droplet containing a partition of a sample. For example, here, an inner droplet 2722 is a reagent droplet comprising reagent 2714 and an outer droplet 2724 is a sample droplet that encloses the inner droplet, and an immiscible, barrier droplet 2726. Immiscible droplet 2726 may be described as an intervening droplet that creates a layer of immiscible fluid 2728 (e.g., an oil 2730) that separates the inner and outer droplets and prevents them from mixing.

Coalescence (also termed fusion) of multiple emulsion 2710 may occur and/or may be induced (such as by heat), indicated at 2732, to form a fused emulsion 2734 of fused droplets 2736. In each fused droplet 2736, the inner and outer droplets have merged within compound droplet 2716 to mix the contents of the inner and outer droplets, such as sample 2712 and reagent 2714, which may create an assay mixture 2738. Also, immiscible droplet 2726 may be enclosed by fused droplet 2736.

Other compound droplets 2716 in the multiple emulsion may split to provide fission, indicated at 2740, instead of fusion. In particular, immiscible droplet 2726 of a compound droplet may fuse with continuous phase 2718, to eject inner droplet 2722 from the compound droplet. As a result, droplets 2722, 2724 may be encapsulated separately by the continuous phase, such that neither droplet 2722 nor 2724 encapsulates the other (i.e., each is outside the other), and such that the sample and reagent of the droplets do not mix. The relative amounts of fusion 2732 or fission 2740 may be adjusted by changing relative droplet sizes, the conditions used to induce coalescence, and/or the composition of dispersed and/or continuous phases, among others.

Each droplet and/or phase may have any suitable fluid composition. Inner droplet 2722 and outer droplet 2724 generally have compositions that are miscible with one another, such as aqueous compositions with water as the at least predominant solvent. In contrast, continuous phase 2718 and immiscible fluid 2728 generally are immiscible with both inner and outer droplets 2722, 2724. Continuous phase 2718 and immiscible fluid 2728 may be miscible with one another and may have the same or distinct compositions. For example, continuous phase 2718 and immiscible fluid 2728 both may be composed predominantly or exclusively of the same liquid chemical compound or mixture of liquid chemical compounds, such as the same oil or mixture of oils. In exemplary embodiments, the continuous phase and/or immiscible fluid is at least predominantly a silicone oil, such as decamethylcyclopentasiloxane.

The emulsion may contain at least one hydrophobic surfactant and/or at least one hydrophilic surfactant. For example, continuous phase 2718 and/or immiscible fluid 2728 may contain at least hydrophobic surfactant, inner droplet 2722 and/or outer droplet 2724 may contain at least one hydrophilic surfactant, or any combination thereof. In some embodiments, the continuous phase and/or the immiscible fluid may include about 0.1-10%, about 1-5%, or about 1% w/w hydrophobic surfactant (e.g., provided by DC 5225C Formulation Aid 2.0 from Dow Corning) in the continuous phase and/or the immiscible fluid. In some embodiments, aqueous phases that are used to form the inner droplets and/or outer droplets may contain about 0.001 to 5% or about 1% w/w hydrophilic surfactant, such as Tween 20 (polyethylene glycol sorbitanmonolaurate, polyoxyethylene sorbitanmonolaurate; HLB 16).

The stability of simple and multiple emulsions against coalescence is a function of the combined properties of type and concentration of surfactant, solvent, temperature, ionic strength, other species that can compete with the surfactants at the water/oil interface, charge, etc. Thus, each of these properties, or combinations thereof, can be selected and/or varied to promote or inhibit coalescence.

Compound droplets 2716 containing sample 2712 and reagent 2714 may be labeled with a code 2746. The code may permit the compound droplets, and fused droplets 2736 formed from the compound droplets, to be mixed with, and distinguished from, other types of compound droplets containing other samples/reagents. The code may be present in inner droplet 2722, outer droplet 2724, barrier droplet 2726, or a combination thereof. The code may be located diffusely in the droplet or may be carried by a particle 2748 (or individually or collectively by two or more particles) that occupies only a portion of the droplet. The code may be optically detectable and may have a predefined optical characteristic, such as an intrinsic optical characteristic, that permits the code to be identified. An exemplary code may be carried by a particle that is fluorescent (e.g., a fluorescent bead, a quantum dot), reflective (e.g., a microfabricated nanobarcode), or the like.

III. SYSTEM OVERVIEW

Figure 2:
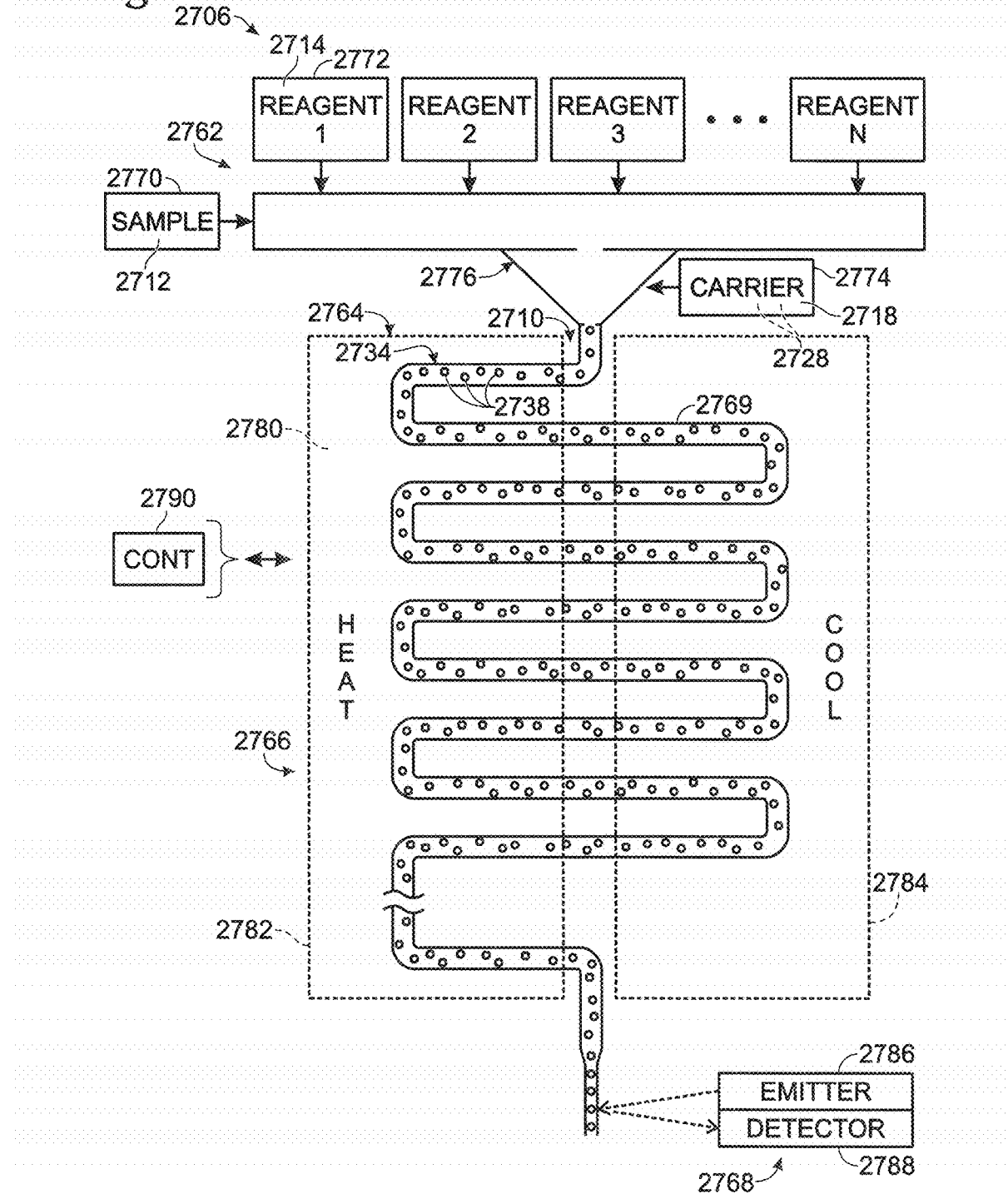
FIG. 2 is a schematic view of an exemplary system (a) for forming and coalescing multiple emulsions and (b) for analyzing assay mixtures produced by coalescence of the multiple emulsions, in accordance with aspects of the present disclosure.

FIG. 2 shows an exemplary system 2760 for forming and coalescing multiple emulsions 2710 and for analyzing assay mixtures 2738 produced by coalescence of the multiple emulsions. The system may include a preparation assembly 2762, a fusion assembly 2764, a processing assembly 2766, and a detection assembly 2768. Fluid generally flows through the system from the preparation assembly to the detection assembly along a flow path provided by at least one channel 2769.

Preparation assembly 2762 may form multiple emulsions from at least one sample 2712 and one or more reagents 2714. The preparation assembly may include at least one sample reservoir 2770 for receiving and holding at least one sample 2712, and one or more reagent reservoirs 2772 for receiving and holding one or more reagents 2714. The preparation assembly also may include one or more other reservoirs 2774 for receiving and holding continuous fluid 2718 and/or immiscible fluid 2728 (see FIG. 1).

The reagents may be controllably associated with the sample(s) through formation of multiple emulsions using at least one droplet generator 2776 of assembly 2762. Droplet generator 2776 may produce a multiple emulsion 2710 from sample 2712, one or more reagents 2714, continuous phase 2718, and immiscible fluid 2728. Each may be driven to the droplet generator by a pump, to produce multiple emulsion 2710. The droplet generator may produce the multiple emulsion from a precursor emulsion formed by the system or formed separately, off-line from the system.

Fusion assembly 2764 may induce coalescence of the multiple emulsion to a fused emulsion 2734 carrying encapsulated assay mixtures 2738. The fusion assembly may include a heater 2780 or other device (e.g., a sonic device, a device that generates an electric field, or the like) that controllably induces coalescence of the multiple emulsion. The fusion assembly may be part of processing assembly 2766 or may be distinct from the processing assembly, such as a device located generally upstream from the processing assembly along channel 2769.

Processing assembly 2766 may subject fused emulsion 2734 to one or more conditions that promote (and/or restrict) reaction of components within assay mixtures 2738. For example, the processing assembly may regulate the temperature of the fused emulsion as the fused emulsion travels through channel 2769 to detection assembly 2768. The processing assembly thus may subject the fused emulsion to an elevated temperature using at least one heating zone 2782, which may stimulate reaction in the fused emulsion. Furthermore, the processing assembly may subject the fused emulsion to repetitive cycles of heating and cooling (i.e., thermal cycling) using alternating travel of the fused emulsion through heating zone(s) 2782 and cooling zone(s) 2784 of the processing assembly. Accordingly, in some embodiments, system 2760 may be used to perform nucleic acid amplification through which the fused emulsion is tested for amplification of a nucleic acid target in individual fused droplets.

Detection assembly 2768 may detect signals from fused droplets during and/or after travel of the fused droplets through processing assembly 2766. The detection assembly may detect one or more signals from individual fused droplets and/or may detect signals collectively from two or more droplets. Accordingly, the fused droplets may be detected individually as each droplet flows past the detection assembly. The detection assembly may detect any suitable optical, electrical, and/or chemical characteristic of a fused droplet. For example, the detection assembly may detect at least one optical characteristic, such as fluorescence intensity, fluorescence resonance energy transfer, fluorescence quenching, fluorescence polarization, fluorescence lifetime, scattering, absorbance, reflectance, or a combination thereof, among others. In some embodiments, the detection assembly may include a light source 2786 that emits light for excitation of fused droplets, and a detector 2788 that measures emitted light from fused droplets.

Formation of multiple emulsions and/or operation of any other aspects of system 2760 may be under the control of a controller 2790. For example, the controller may control reagent and sample selection, flow rates (i.e., pump speeds), selection and/or operation of a droplet generator (e.g., droplet size, generation rate, etc.), temperature and/or size of heating and/or cooling zones (e.g., heating/cooling profiles), operation of the detection assembly, data collection, data processing, operation of a user interface, or any combination thereof, among others.

Figure 3:
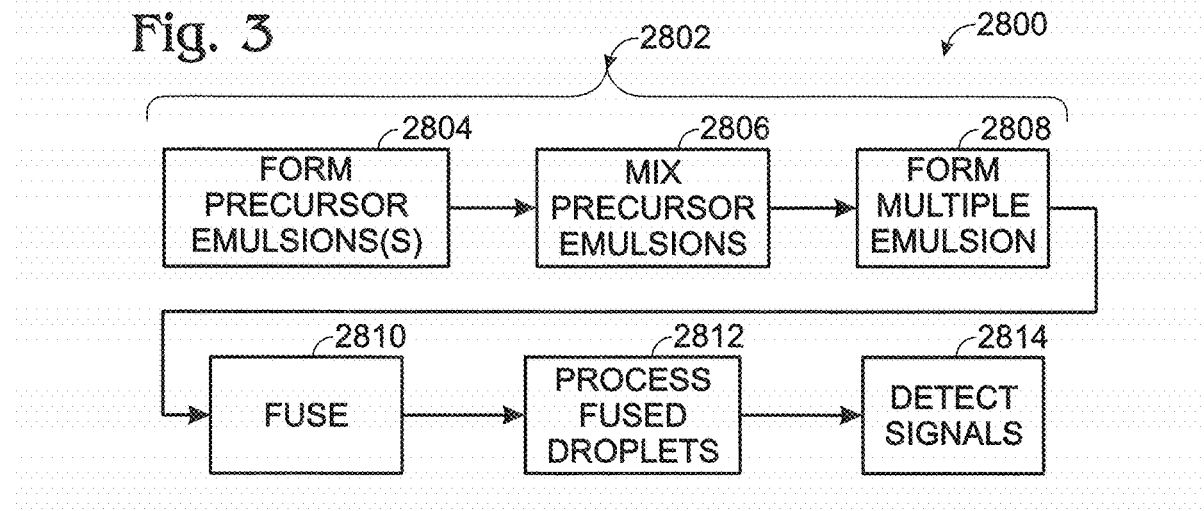
FIG. 3 is a flowchart of an exemplary method of testing one or more samples using a multiple emulsion, in accordance with aspects of the present disclosure.

FIG. 3 shows an exemplary method 2800 of analyzing one or more samples using a multiple emulsion. The method may include any combination of the steps shown, performed in any suitable order, with each step being performed one or more times. The method may be utilized to perform the same test on a given sample/reagent combination in a plurality of fused droplets. Alternatively, the method may be utilized, particularly with aid of distinguishing codes, to perform the same test on a plurality of samples, a plurality of different tests on the same sample, or a plurality of different tests on a plurality of different samples.

A multiple emulsion may be obtained, indicated at 2802. The multiple emulsion may be formed, at least partially, by a sample analysis system, such as system 2760 described above, or may be formed at least partially or completely off-line from the sample analysis system. Obtaining a multiple emulsion may include any combination of forming a precursor emulsion (or two more precursor emulsions), indicated at 2804, mixing precursor emulsions, indicated at 2806, and forming a multiple emulsion from the mixed (or unmixed) precursor emulsion(s), indicated at 2808.

One or more precursor emulsions may be formed. Each precursor emulsion may be a double (or greater) emulsion containing a plurality of inner droplets each encapsulated by a respective barrier droplet. The inner droplets may contain a sample and/or a reagent and, optionally, may include an identifying code that can be detected and correlated with the sample/reagent for identification. The precursor emulsions may be formed by a sample analysis system or may be formed off-line from the system, such as on a larger scale at a centralized facility for distribution to users. In the latter case, the precursor emulsions may include commonly used reagents, such as PCR reagents, that a user could combine with user-generated sample emulsions.

Two or more precursor emulsions may be mixed to create a mixture of precursor emulsions. The mixture may include inner droplets of distinct types containing respective distinct samples and/or distinct reagents. The inner droplets of distinct types may (or may not) be distinguishable via a corresponding, predefined code included in each distinct type of inner droplet. In some embodiments, only one precursor emulsion may be utilized to form each multiple emulsion.

A multiple emulsion may be formed from the mixed (or unmixed) precursor emulsion(s). The multiple emulsion may be a triple (or greater) emulsion containing a plurality of compound droplets, with each compound droplet containing an inner droplet encapsulated by a barrier droplet, which, in turn, is encapsulated by an outer droplet. The inner droplets, if formed from a mixed precursor emulsion, may be of at least two types that respectively include partitions of at least two distinct samples, of at least two distinct reagents, or both. Optionally, the multiple emulsion further may be mixed with one or more other multiple emulsions, particularly when distinguishing codes are incorporated into compound droplets of the multiple emulsions.

The multiple emulsion may be fused, indicated at 2810, to form a fused emulsion. Fusion of the multiple emulsion may occur spontaneously, such that no treatment, other than a sufficient time delay (or no delay), is necessary before processing fused droplets. Alternatively, the multiple emulsion may be treated to controllably induce fusion of droplets to form assay mixtures. The treatment may include heating/cooling to change temperature, applying pressure, altering composition (e.g., via a chemical additive), applying acoustic energy (e.g., via sonication), exposure to light (e.g., to stimulate a photochemical reaction), applying an electric field, or any combination thereof. The treatment may be continuous or may vary temporally (e.g., pulsatile, shock, and/or repetitive treatment). The treatment may provide a gradual or rapid change in an emulsion parameter, to effect steady state or transient initiation of droplet fusion. In any event, the stability of the multiple emulsion, and its responsiveness to a treatment to induce droplet fusion, may be determined during its formation by selection of an appropriate surfactant type, surfactant concentration, critical micelle concentration, ionic strength, etc., for one or more phases of the multiple emulsion.

The fused emulsion may be processed, indicated at 2812. Processing may include subjecting the fused emulsion to any condition or set of conditions under which at least one reaction of interest can occur (and/or is stopped), and for any suitable time period. Accordingly, processing may include maintaining the temperature of the fused emulsion near a predefined set point, varying the temperature of the fused emulsion between two or more predefined set points (such as thermally cycling the fused emulsion), exposing the fused emulsion to light, changing a pressure exerted on the fused emulsion, adding at least one chemical substance to the fused emulsion, applying an electric field to the fused emulsion, or any combination thereof, among others.

Signals may be detected from the fused emulsion after and/or during processing, indicated at 2814. The signals may be detected optically, electrically, chemically, or a combination thereof, among others. The detected signals may include test signals that correspond to at least one reaction of interest performed in the fused emulsion. Alternatively, or in addition, the detected signals may include code signals that correspond to codes present in the fused emulsion. Test signals and code signals generally are distinguishable and may be detected using the same or distinct detectors. For example, the test signals and code signals each may be detected as fluorescence signals, which may be distinguishable based on excitation wavelength (or spectrum), emission wavelength (or spectrum), and/or distinct positions in a fused droplet (e.g., code signals may be detectable as more localized than test signals with respect to fused droplets), among others. As another example, the test signals and code signals may be detected as distinct optical characteristics, such as test signals detected as fluorescence and code signals detected as optical reflectance. As a further example, the test signals may be detected optically and the code signals electrically, or vice versa.

Data corresponding to the detected signals may be processed. Data processing may assign an assay result to each assay mixture (fused droplet) analyzed, which may be an analog or digital value. In some embodiments, the digital value may be binary, corresponding to a positive or negative test for an analyte in the assay mixture. Also, or in addition, data processing may identify a sample/reagent present in each assay mixture (fused droplet) by correlating code signals with a predefined code and/or with a sample/reagent associated during emulsion formation with the predefined code. Also, one or more test signals may be correlated with the identified sample/reagent to assign a test result to the identified sample/reagent.

IV. FORMATION AND MIXING OF PRECURSOR EMULSIONS

Figure 4:
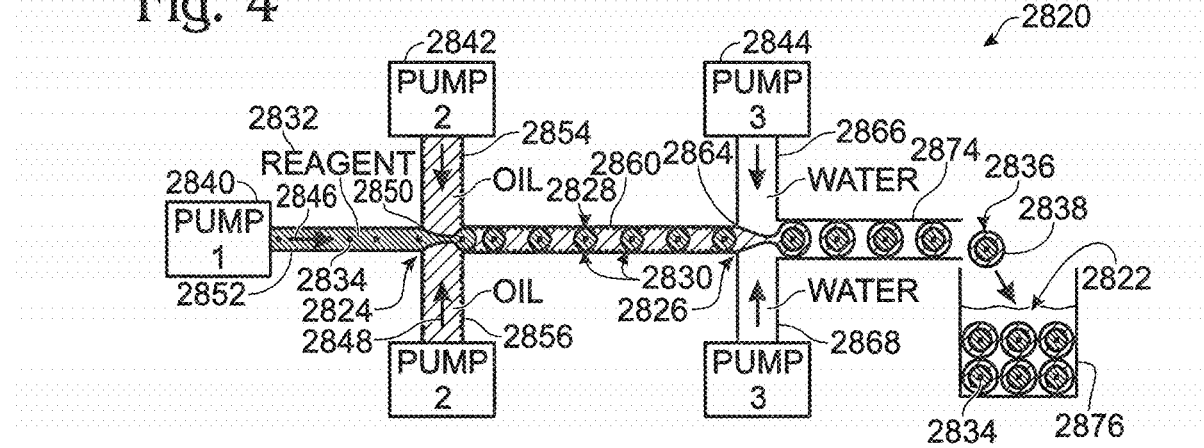
FIG. 4 is a schematic view of an exemplary device for forming a precursor emulsion that can be modified to create a multiple emulsion, in accordance with aspects of the present disclosure.

FIG. 4 shows an exemplary device 2820 for forming a precursor emulsion 2822. Device 2820 may be equipped with a plurality of droplet generators arranged in series, such as a first droplet generator 2824 and a second droplet generator 2826.

The droplet generators may create inner and outer droplets of precursor emulsion 2822 serially. The first droplet generator 2824 may form a single emulsion 2828 of reagent droplets 2830 (i.e., future inner droplets 2722 of a compound emulsion (see FIG. 1)), with each reagent droplet containing a reagent 2832 and, optionally, a code 2834. In other embodiments, the first droplet generator 2824 may form a single emulsion of sample droplets. Second droplet generator 2826, in turn, may form precursor emulsion 2822 (a double emulsion) from single emulsion 2828. In particular, the second droplet generator may create compound droplets 2836 in which reagent droplets 2830 and code 2834 are encapsulated by larger droplets 2838 (i.e., future barrier droplets 2726 of a multiple emulsion (see FIG. 1)). In exemplary embodiments, singe emulsion 2828 may be described as a water-in-oil (W/O) emulsion and precursor emulsion 2822 may be described as a water-in-oil-in-water (W/O/W) emulsion according to the predominant fluid in each phase.

Each droplet generator may be supplied with fluid streams driven by pumps 2840-2844. For example, here, three pumps supply fluid to first and second droplet generators 2824, 2826. However, any suitable number of pumps may be utilized to drive fluid. Exemplary pumps that may be suitable are positive displacement pumps (e.g., syringe pumps), which can be used to drive fluids at desired flow rates (e.g., 1 nL-100 µL/min) through the fluidic flow paths. The ratio of the flow rates to each droplet generator may be adjustable to create droplets of the desired size (diameter) and frequency.

First droplet generator 2824 may receive a feed stream 2846 and at least one encapsulating stream 2848. The streams may be received at a junction 2850 (e.g., a four-way or cross junction). The junction of a droplet generator formed at a fluidic intersection may be a flow-focusing junction that produces droplets. Junction 2850 may be formed at an intersection of a feed channel 2852 and cross channels 2854, 2856. The feed channel may carry feed stream 2846 to junction 2850, driven by first pump 2840. One or more cross channels may carry one or more encapsulating streams 2848 of oil to junction 2850 driven by second pump 2842. Feed stream 2846 may be an aqueous stream containing reagent 2832 and code 2834. For example, reagent 2832 may include at least one primer (or a pair of primers) for amplifying a nucleic acid target. The feed stream and/or encapsulating streams described here and elsewhere in the present disclosure may include a surfactant, such as high and low HLB surfactants, respectively, or vice versa. Single emulsion 2828 may flow from junction 2850 as an outflow stream carried in an outflow channel 2860.

Outflow channel 2860 may function as a feed channel for second droplet generator 2826. Thus, the outflow stream may serve as a feed stream for second droplet generator

2826. The feed stream may be encapsulated at a junction 2864 (e.g., another four-way junction) formed at the intersection of outflow channel 2860 and cross channels 2866, 2868, which carry encapsulating streams. The encapsulating streams may be an aqueous phase (labeled here as "water"), which may include salt(s), buffer(s), and/or surfactant(s) (e.g., a hydrophilic surfactant), among others. Accordingly, reagent droplets 2830 may be encapsulated at the second droplet generator by a barrier droplet of immiscible liquid, such as oil, which in turn may be disposed in an aqueous continuous phase. Precursor emulsion 2822 may flow from junction 2864 in an outflow channel 2874 and may be stored in a reservoir 2876.

Precursor emulsion 2822 may be stored individually or as a mixture (see below). In either case, the concentration of compound droplets may be concentrated over time by gravity using a density difference between the droplets and the continuous phase. Concentrating the droplets may be beneficial for minimizing the dilution of aqueous sample in downstream processing steps.

As each W/O/W emulsion created by the device of FIG. 4 can be labeled with a unique code, individual W/O/W emulsions can be mixed to create a panel or library of the desired combination of reagents against which a sample can be screened (or vice versa).

Device 2820 may comprise channels (e.g., any combination of channels 2852-2856, 2860, 2866, 2868, 2874) with internal diameters ranging from about 1-500 microns or about 20-250 microns, among others. The internal diameters of the channels may correspond to the diameter of droplets to be generated. For example, first outflow channel 2860 may have an internal diameter corresponding to the desired diameter of reagent droplets 2830, and second outflow channel 2874 may have an internal diameter corresponding to the desired diameter of larger droplets 2838. Thus, the internal diameter of the first outflow channel may be smaller than that of the second outflow channel. In exemplary embodiments, intended for illustration only, the diameters of feed channel 2852 and first outflow channel 2860 may be about the same, such as about fifty micrometers. In contrast, the diameter of second outflow channel 2874 may be about 100 micrometers.

The hydrophobic/hydrophilic character of interior surfaces of device 2820 may be important to the function of the device. Generally, interior surfaces in contact with a hydrophilic fluid, such as water, are hydrophilic, and interior surfaces in contact with a hydrophobic fluid, such as oil, are hydrophobic. For example, in FIG. 4, interior surfaces of channels that carry an aqueous stream are hydrophilic (e.g., the interior surfaces of channels 2852, 2866, 2868, and 2874) and are shown as a solid line. In contrast, interior channel surfaces that carry a hydrophobic stream (e.g., oil) are hydrophobic (e.g., the interior surfaces of channels 2854, 2856, and 2860) and are indicated with a dashed line at the interior surface. With this selection of hydrophilic and hydrophobic interior surfaces, a feed stream entering a junction of a droplet generator cannot wet the surfaces of the cross channels or the outflow channel of the junction. Also, the exterior surfaces of droplets cannot wet the surfaces of channels through which the droplets flow, thereby preventing destabilization of the emulsion.

Flow paths of device 2820 may be formed by any suitable process. For example, the channels may be capillaries formed by capillary tubing. Capillaries can be connected using microfluidic cross and/or T connectors (e.g., Labsmith, Livermore, Calif.). Alternatively, any of the flow paths can be constructed using microfabrication processes such as photolithography, hot embossing, injection molding, or a combination thereof, among others.

In exemplary embodiments, flow paths of device 2820 can be constructed from fused silica capillary tubes that are hydrophilic (e.g., having an Si—OH surface functionality). Surfaces of the capillary tubes can be rendered hydrophobic by applying a coating (e.g., a covalent coating using an organosilane such as those commercially available for glass treatment (e.g., Aquapel (PPG Industries))). A single capillary tube can be modified to have regions of the desired hydrophilicity/hydrophobicity. For example, an end of the capillary tube can be rendered hydrophobic by dip coating the tube in Aquapel for one minute while simultaneously passing air through the tube. This creates one hydrophobic end, and a hydrophilic flow channel and end. A capillary tube can be rendered completely hydrophobic by, for example, passing Aquapel through the capillary tube for one minute, followed by air and allowing the capillary tube to dry. Once dry, an end of the capillary tube can be cleaved to expose a hydrophilic end.

Figure 5:
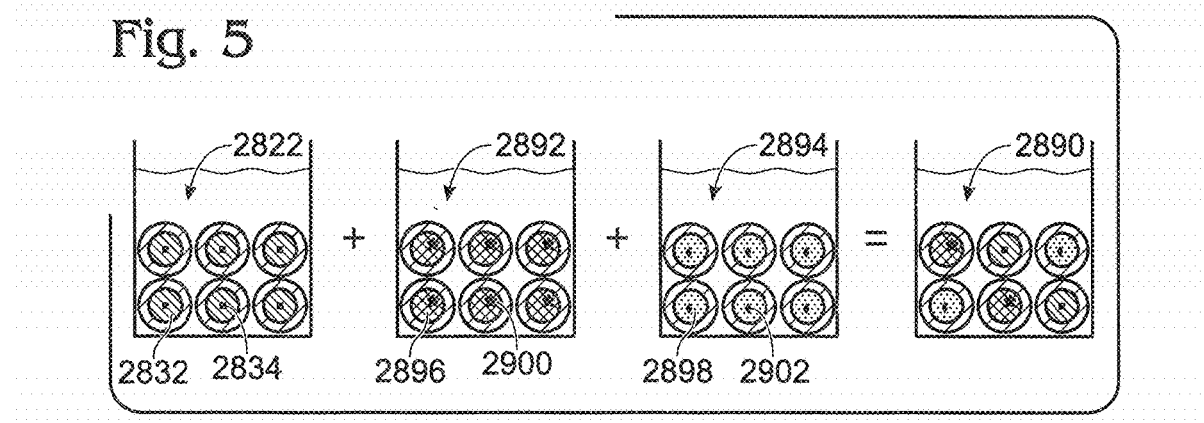
FIG. 5 is a schematic view of an exemplary composition formed by mixing precursor emulsions of different types, in accordance with aspects of present disclosure.

FIG. 5 is a schematic view of an exemplary composition 2890 formed by mixing a plurality of precursor emulsions 2822, 2892, 2894 of different types. Each precursor emulsion may be a water-in-oil-in-water (W/O/W) emulsion. Each precursor emulsion may contain a distinct sample and/or a distinct reagent and may be labeled with a corresponding, distinct, predefined code. For example, each precursor emulsion may include a different primer pair and probe for a corresponding different nucleic acid target to be amplified. Here, three emulsions, each including a distinct reagent (2832, 2896, and 2898) and a corresponding distinct code (2834, 2900, and 2902, respectively), are mixed as an illustration, but in other embodiments, any suitable number of precursor emulsions and thus any suitable number of different droplet types, different reagents, different samples, and/or different codes may be combined. Each precursor emulsion may be formed using any suitable device, such as device 2820 of FIG. 4, by changing the input of reagent (2832, 2896, or 2898) (and/or sample) and code (2834, 2900, or 2902) in the feed stream flowing to the first droplet generator.

V. FORMATION AND COALESCENCE OF A MIXED EMULSION

Figure 6:
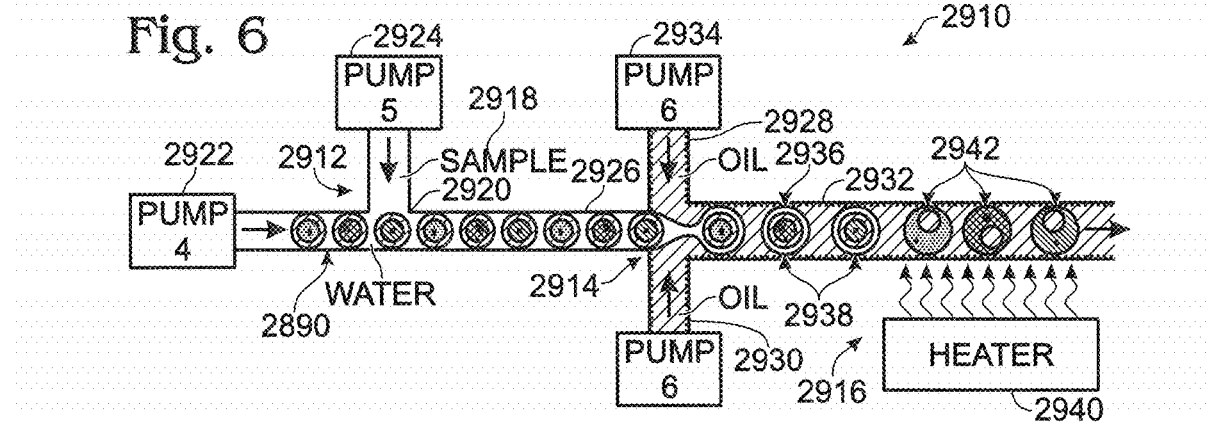
FIG. 6 is a schematic view of an exemplary device for creating and coalescing multiple emulsions, with the device (a) transforming a coded mixture of precursor emulsions into a multiple emulsion and (b) fusing inner and outer droplets of compound droplets within the multiple emulsion, in accordance with aspects of present disclosure.

FIG. 6 shows a schematic view of an exemplary device 2910 for forming and fusing a multiple emulsion. The device may be equipped with a sample input region 2912, a droplet generator 2914, and a fusion region 2916, among others. Device 2910 may be connected to another device that generates precursor emulsions (e.g., device 2820 of FIG. 4) or may have no physical connection to such a device. Also, device 2910 may be part of a sample analysis system (e.g., providing at least a portion of preparation assembly 2762 and/or fusion assembly 2764 of system 2760 of FIG. 2) or may have no physical connection to a sample analysis system.

Sample input region 2912 may mix a sample 2918 (and/or a reagent) with a precursor emulsion. The precursor emulsion may be one precursor emulsion (e.g., precursor emulsion 2822) or a mixture of precursor emulsions (e.g., composition 2890). Here, composition 2890 generated in FIG. 5 is used to illustrate operation of device 2910. Composition 2890 and an aqueous sample 2918 may be mixed at a fluidic junction 2920 supplied by fluid streams of precursor emulsion and sample driven by respective pumps 2922, 2924. Mixing is shown here as being performed by device 2910, but, alternatively, precursor emulsion(s) and sample may be mixed off-line from the device. Mixing on-line may be beneficial to achieve uniform spacing of input droplets of the precursor emulsion in the fluidic flow channel. The continuous phase of the precursor emulsion and the sample both may be aqueous, to enable mixing.

Droplet generator 2914 may have any of the features disclosed above for the droplet generators of FIG. 4. For example, droplet generator 2914 may be structured generally like first droplet generator 2824. In particular, droplet generator 2914 may include a hydrophilic feed channel 2926 (shown with a solid interior surface) carrying an aqueous continuous phase. Droplet generator 2914 also may include hydrophobic cross channels 2928, 2930 carrying an immiscible liquid, such as oil, and further may include a hydrophobic outflow channel 2932 (with each hydrophobic surface shown with a dashed line). Outflow channel 2932 may have an inner diameter that is greater than feed channel 2926 and/or greater than the diameter of precursor emulsion droplets. In particular, outflow channel 2932 may have an inner diameter that corresponds to the desired size of compound droplets to be formed. In exemplary embodiments, intended for illustration only, the diameter of feed channel 2926 may be about 100 micrometers. In contrast, the diameter of outflow channel 2932 may be about 150 micrometers. Also, the aqueous continuous phase and/or the immiscible liquid may include a surfactant as described elsewhere in the present disclosure.

A pump 2934, in conjunction with pumps 2922, 2924, may create a confluence of the feed stream and the oil streams at a fluid junction of the droplet generator. As a result, sample and double droplets (a W/O/W multiple emulsion) flowing in the feed stream may be co-encapsulated by oil to form a W/O/W/O multiple emulsion 2936 in outflow channel 2932. Here, multiple emulsion 2936 is shown as a mixture of different types of coded compound droplets 2938 containing the same sample and different reagents and codes (also see FIG. 5).

The frequency of lower-order droplets (e.g., single or double droplets) arriving at a droplet generator (e.g., droplet generator 2914 in FIG. 6 or droplet generator 2824 of FIG. 4) may be adjusted to correspond to the frequency of higher-order droplets (e.g., double or triple droplets, respectively) leaving the droplet generator. In other words, the frequency of entry and exit may be about the same to achieve uniform higher-order droplets. These frequencies can be controlled by adjusting flow rate ratios of feed and encapsulating streams and the concentration (i.e., the spacing) of lower-order droplets in the feed stream, to ensure that the timing of lower-order droplet arrival at the droplet generator coincides with the frequency of droplet formation.

Fusion region 2916 may include a heater 2940 that applies heat at a desired time to multiple emulsion 2936. The applied heat may induce fusion within compound droplets of the multiple emulsion to form fused droplets 2942 (also see FIG. 1). The fused droplets may result from mixing of an inner droplet with an outer droplet of individual compound droplets. For example, a W/O/W/O emulsion may be converted to an O/W/O emulsion, in which previously isolated sample and reagent are merged as a coded mixture of sample and reagent. The fused droplets then may be processed further, such as by thermal cycling to promote amplification (e.g., PCR) and signal detection from the processed droplets.

Figure 7:
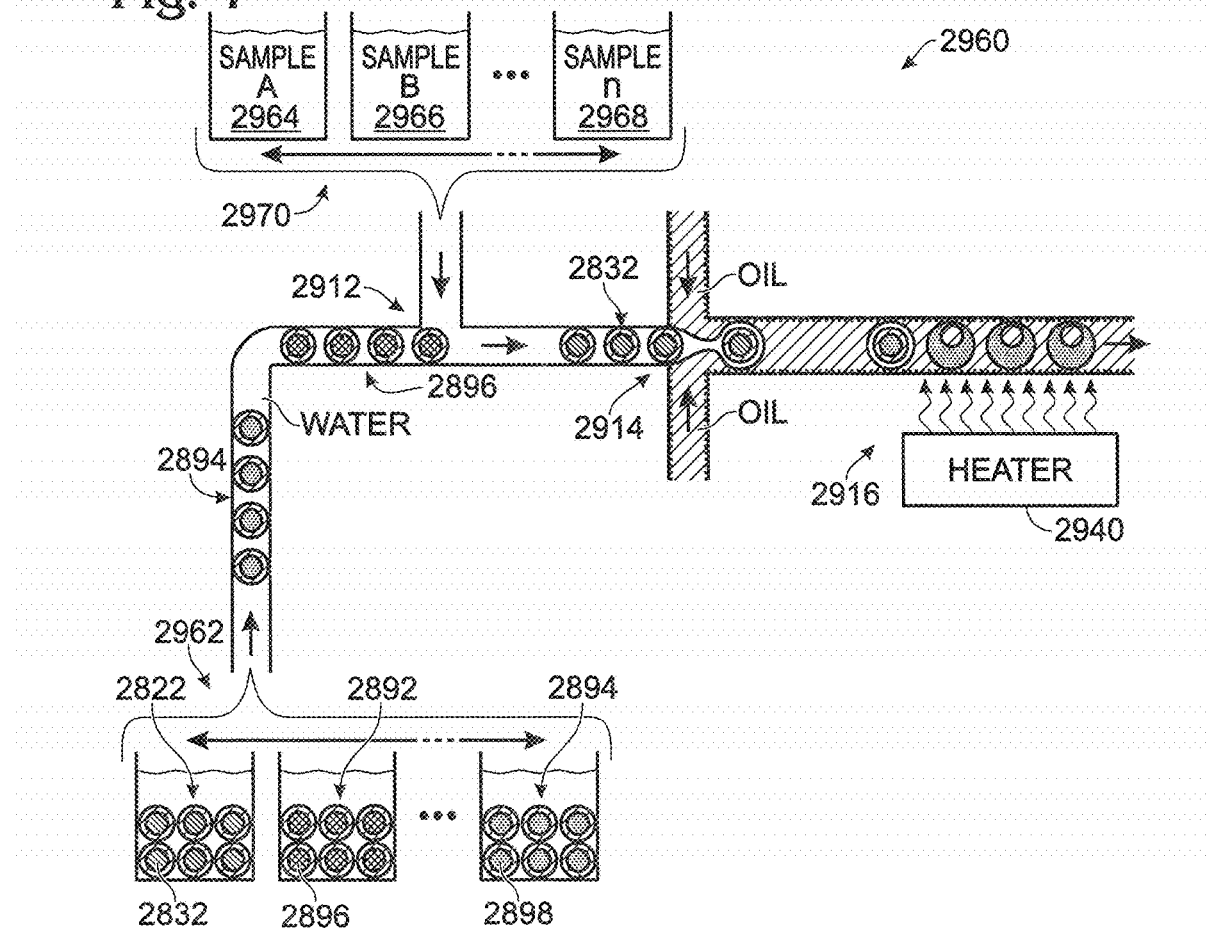
FIG. 7 is a schematic view of another exemplary device for creating and coalescing multiple emulsions, with the device in the process of (a) transforming individual precursor emulsions serially into spatially and temporally resolved multiple emulsions and (b) fusing inner and outer droplets of compound droplets within each multiple emulsion, in accordance with aspects of present disclosure.

FIG. 7 shows another exemplary device 2960 for creating and coalescing multiple emulsions. Device 2960 may be constructed generally like device 2910 of FIG. 6, with equivalent elements, such as droplet generator 2914 and fusion region 2916, labeled as in FIG. 6. Pumps are omitted from FIG. 7 to simplify the presentation. Device 2960 may be connected to another device that generates precursor emulsions (e.g., device 2820 of FIG. 4) or may have no physical connection to such a device. Also, device 2960 may be part of a sample analysis system (e.g., providing at least a portion of preparation assembly 2762 and/or fusion assembly 2764 of system 2760 of FIG. 2) or may have no physical connection to a sample analysis system. In any event, fused droplets generated by device 2960 may be used in amplification assays.

Device 2960 may be utilized to create and coalesce distinct multiple emulsions in a spatially and temporally separated manner. In other words, distinct multiple emulsions may be created serially such that different multiple emulsions (and fused emulsions formed therefrom) are distinguishable and identifiable based on their different times of formation and different positions along the flow path of the device (and/or along a flow path of a system in which the device is integrated). Thus, distinct emulsions may exit device 2960 separately and/or may arrive separately at a downstream detector (e.g., detection assembly 2768 of FIG. 2).

Device 2960, like device 2910 of FIG. 6, is shown further encapsulating precursor emulsions at droplet generator 2914. However, in FIG. 7, precursor emulsions 2822, 2892, and 2894 are not mixed before entry into device 2960. Instead, droplets of each precursor emulsion flow to droplet generator 2914 as a group that is spaced along the flow path from other groups of precursor droplets. In other words, there may be a physical and temporal gap between each group of precursor droplets that flows past sample input region 2912. Accordingly, droplets of precursor emulsions 2822, 2892, and 2894, and higher-order multiple emulsions produced therefrom, can be tracked and identified without the use of codes (e.g., codes 2834, 2900, and 2902 shown in FIGS. 4-6).

Various combinations of reagent and sample may be associated with one another in multiple emulsions based on when each is introduced into the flow path. Precursor emulsions 2822, 2892, and 2894 may be introduced individually and selectably into the flow path using a selector 2962. Similarly, a sample (e.g., any of samples 2964, 2966, 2968) may be associated individually and selectably with each precursor emulsion by input of the sample coincident with each precursor emulsion, via sample input region 2912. The sample may be selected from a set of samples using another selector 2970. Accordingly, each type of multiple emulsion (and fused emulsion formed therefrom) can be identified temporally and/or spatially according to its position along the flow path. Each selector 2962, 2970 may, for example, be a multi-port valve or an autosampler, among others.

FIG. 7 shows a library of pre-encapsulated reagents (2832, 2896, 2898; e.g., a primer library) being further encapsulated individually by a continuous phase that includes a sample, which may be selectable from a library of samples. However, the relative positions of the reagents and samples may be switched. In other words, the samples may be pre-encapsulated to form a library of samples, which may be further encapsulated individually by a continuous phase that includes a reagent, which may be selectable from a library of reagents (e.g., a primer library).

VI. MULTIPLE EMULSIONS PROVIDING FUSION OF INNER DROPLETS WITH ONE ANOTHER

FIG. 8 shows a diagram illustrating exemplary coalescence of another multiple emulsion 2990 to achieve mixing of small volumes of a sample 2992 and a reagent 2994 within compound droplets of the emulsion. Here, two or more inner droplets 2996 fuse within a compound droplet, rather than inner and outer droplets fusing within a compound droplet (see FIG. 1). In particular, at least one sample droplet 2998 comprising at least one partition of sample 2992 and at least one reagent droplet 3000 comprising at least one reagent 2994 are fused, indicated at 3002, (e.g., fusion induced by application of heat) to form at least one fused droplet 3004 that provides a mixture of sample and reagent for performing an assay, such as a nucleic acid assay (e.g., nucleic acid amplification in fused droplets).

Multiple emulsion 2990 may include a plurality of compound droplets disposed in a continuous carrier phase 3006, namely, an immiscible fluid or liquid, (e.g., water in this example). (Only one compound droplet 3008 of the multiple emulsion is shown here to simplify the presentation.) Each compound droplet 3008 may include an outer droplet or barrier droplet 3010 that is immiscible with carrier phase 3006. For example, here, barrier droplet comprises oil to create a layer of immiscible fluid that separates inner droplets 2996 and, optionally, restricts their ability to fuse with each other until fusion is induced. Thus, barrier droplet 3010 may encapsulate each of the inner droplets of a compound droplet. In some embodiments, emulsion 2990 may be a water-in-oil-in-water (W/O/W) emulsion.

Compound droplet 3008 may comprise any suitable number of inner droplets. In some embodiments, the compound droplet may comprise an average of about one, two, or more inner droplets, or an average of at least about one, two, five, ten, twenty, one-hundred, or more of each type of inner droplet. The use of a larger number of inner droplets in a compound droplet may reduce statistical variation in the total volume of sample and reagent in each compound droplet and/or may reduce statistical variation in the ratio of sample droplet to reagent droplet volumes within each compound droplet, thereby producing a greater number of fused droplets and assay mixtures containing sample and reagent. The average ratio of sample droplets to reagent droplets (by number or volume) may be the same or different. If two or more reagents droplets are present in the compound droplet, the reagent droplets may have the same or different compositions. Accordingly, a compound droplet may contain two or more distinct types of reagent droplets, to permit creation of a larger number of combinations of reagents in fused droplets from a smaller number of reagent emulsions.

A subset of the compound droplets in a multiple emulsion, due to statistical variation, may be deficient and thus unsuitable for performing tests. For example, these deficient compound droplets may contain no sample droplet, no reagent droplet, a ratio of sample droplets to reagent droplets that is outside of an acceptable range, or a combination thereof. Furthermore, in some compound droplets, fusion of sample and reagent droplets may not occur. Thus, measurements performed on compound droplets after fusion may be filtered to exclude data from compound droplets lacking a correct mixture of sample and reagent. Alternatively, background signals caused by these deficient compound droplets may be acceptable. In some embodiments, one or more labels or markers may be disposed in sample and reagent droplets to permit fused droplets containing sample and reagent to be distinguished from other inner droplets (e.g., by optical and/or electrical detection).

FIG. 9 shows an exemplary device 3020 for forming a precursor emulsion of reagent droplets 3000 (e.g., primer droplets containing at least one primer or a pair of primers), which can be modified with sample droplets to create multiple emulsion 2990 of FIG. 8. Device 3020 may include a droplet generator 3022 that creates the reagent droplets from a reagent stream 3024 of at least one reagent. For example, reagent stream 3024 may contain an aqueous composition of one or more primers, such as a mixture of primers for amplification of a particular nucleic target. Reagent stream 3024 may meet one or more streams 3026 of an immiscible carrier fluid (e.g., oil) at a junction 3027 of the droplet generator, to generate reagent droplets 3000. The reagent droplets may be collected as a reagent emulsion 3028 in a container or vessel such as a well 3029, which may be part of any array of containers or vessels (e.g., a microplate) to provide a library of reagents. The reagent composition and/or the immiscible carrier fluid may include one or more surfactants as described elsewhere in the present disclosure.

FIG. 10 shows an exemplary device 3030 for forming a precursor emulsion of sample droplets 2998, which can be modified with reagent droplets to create multiple emulsion 2990 of FIG. 8. Device 3030 may include a droplet generator 3032 that creates sample droplets from partitions of a sample stream 3034. The sample stream may be formed of an aqueous composition including a sample or sample aliquot. In any event, compositions forming reagent stream 3024 (see FIG. 9) and sample stream 3034 may be composed of miscible fluids. Sample stream 3034 may meet one or more streams 3036 of an immiscible carrier fluid (e.g., oil) at a junction 3037 of the droplet generator, to generate sample droplets 2998. The sample droplets may be collected as a sample emulsion 3038 in a container or vessel, such as a well 3039, which may be part of any array of containers or vessels (e.g., a microplate) to provide a library of samples. The sample stream and/or the immiscible carrier fluid may include one or more surfactants as described elsewhere in the present disclosure. The sample droplets and the reagent droplets each may be present in a water-in-oil (W/O) emulsion.

FIG. 11 shows a schematic view of an exemplary system 3050 for forming a reagent library (e.g., primary library 3052) of different reagent emulsions 3028 and a sample library 3054 of different sample emulsions 3038, each disposed in a respective array. System 3050 may include one or a plurality of devices 3020 and/or devices 3030 (see FIGS. 9 and 10) to provide droplet generators ("DG") 3022, 3032 that receive reagents (e.g., primer pairs 1 to n) and samples (e.g., samples 1 to n) and create a separate emulsion of reagent droplets or of sample droplets from each reagent or sample. The same droplet generator or different droplet generators may be used to generate different members of each respective library and/or different members of different libraries. In any event, each reagent emulsion 3028 or sample emulsion 3038 may be stored at a known address in an array, such as an array formed by a microplate 3056, to permit retrieval of droplets of a selected emulsion on demand. Any suitable number of different samples and reagents may be placed in each array. For example, each of the reagent array and the sample array may be a respective reagent library or sample library of two or more separate members and the number of members in the reagent library and the sample library may be different. Alternatively, only one sample emulsion or reagent emulsion may be formed. Furthermore, in some embodiments, the reagent library and/or the sample library may be prepared off-line from (or on-line with) a sample analysis system (e.g., see FIG. 2).

FIG. 12 shows a schematic view of an exemplary device 3060 for creating and coalescing multiple emulsions. Device 3060 may permit selection of (a) any reagent droplets 3000 from any one (or more) of the different reagent emulsions (3028) of the primer library, for combination with (b) any sample droplets 2998 from any one (or more) of the different sample emulsions (3038) of the sample library. Stated differently, the use of multiple emulsions formed from arrays of precursor emulsions enables a dynamic platform that permits combination of any reagent and any sample in the arrays on demand, that is, at any time, since the system can switch quickly from one combination to another.

A selected combination of reagent and sample droplets may be removed from their respective arrays, by operation of a selector 3062, and introduced into respective channels 3064, 3066 that meet at a junction 3068 (e.g., a microfluidic junction), to form a confluence of reagent and sample streams. Selector 3062 may be any device that transfers at least a portion of a reagent emulsion and/or of a sample emulsion and/or that regulates such transfer. The selector may, for example, be a multi-port connection between an emulsion array and channel 3064 and/or 3066 and/or an auto-sampler (e.g., an automated pipette device), among others.

Streams of reagent droplets 3000 and sample droplets 2998 may flow from junction 3068 in a combined sample/reagent stream 3070 to a droplet generator 3072. The droplet generator may create compound droplets 3074 disposed in a continuous phase (e.g., an aqueous continuous phase). Each compound droplet 3074 may, on average, contain a plurality of inner droplets including at least one sample droplet 2998 and at least one reagent droplet 3000. The inner droplets may be encapsulated by a barrier droplet 3076 formed of a fluid that is immiscible with the continuous phase and with the inner droplets. The average number of sample droplets and reagent droplets contained in each compound droplet may be determined (and adjusted) by the size sample/reagent droplets, the ratio and density of these types of droplet in stream 3070, the size of the barrier droplet formed, and the like.

Compound droplets 3074 may travel through a heating zone formed by a heater. Application of heat may induce fusion of the inner droplets to form fused droplets 3078 from sample and reagent droplets. The fusion may result in transformation of a plurality of inner droplets to one inner droplet within a compound droplet. Alternatively, the fusion may fail or be incomplete in some compound droplets, such that two or more inner droplets remain in a compound droplet after fusion of other compound droplets is complete.

In any event, the fused droplets may be separated from the continuous phase by barrier droplet 3076. Proper selection of surfactants permits fusion of the inner droplets with one another much more efficiently than fusion of the inner droplets with the continuous phase.

Each fused droplet may include an assay mixture created by mixing the contents of at least one sample droplet and at least one reagent droplet. For example, the assay mixture may be capable of amplification of a nucleic acid target, if present, in the fused droplet.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of sample analysis, comprising:
   forming a first type and a second type of reagent droplets, wherein the first type has a first code and the second type has a second code to identify each type;
   encapsulating the first and second types of reagent droplets in sample droplets; and
   inducing fusion of the sample droplets with the encapsulated first and second types of reagent droplets to produce fused droplets each having the first code or the second code.

2. The method of claim 1, wherein the first type and the second type of reagent droplets respectively contain a first pair of primers for amplification of a first nucleic acid target and a second pair of primers for amplification of a second nucleic acid target, and wherein the sample droplets contain nucleic acid.

3. The method of claim 1, wherein each code is provided by at least one particle in each type of reagent droplet.

4. The method of claim 1, wherein the step of inducing fusion includes a step of heating the first and second types of reagent droplets and the sample droplets after the step of encapsulating.

5. The method of claim 1, wherein the step of inducing fusion includes a step of applying an electric field to the first and second types of reagent droplets and the sample droplets after the step of encapsulating.

6. The method of claim 2, wherein the fused droplets contain a respective probe for each nucleic acid target and a thermostable polymerase, further comprising a step of thermally cycling the fused droplets after the step of inducing fusion.

7. The method of claim 6, further comprising a step of collecting data from a label of each respective probe after the step of thermally cycling.

8. The method of claim 7, wherein the step of collecting data includes a step of detecting fluorescence from the label of each respective probe present in a plurality of the fused droplets.

9. The method of claim 7, further comprising a step of determining a concentration of each nucleic acid target using the collected data.

10. The method of claim 7, wherein the step of collecting data includes a step of detecting test signals, further comprising (a) a step of detecting code signals from the fused droplets and (b) a step of utilizing the code signals to correlate test signals with the first and second types of reagent droplets.

11. The method of claim 10, wherein the step of utilizing the code signals includes a step of correlating test signals with a presence of the first and second nucleic acid targets in the fused droplets.

12. A method of sample analysis, comprising:
   obtaining an emulsion including a plurality of outer droplets disposed in a liquid carrier phase and each encapsulating at least one inner droplet, wherein the outer droplets are sample-containing droplets and the at least one inner droplet is at least one reagent-containing droplet or wherein the outer droplets are reagent-containing droplets and the at least one inner droplet is at least one sample-containing droplet; and heating the emulsion to induce fusion of the outer droplets with the at least one inner droplet to form fused droplets that combine sample and reagent to create assay mixtures for performing an assay.

13. The method of claim 12, wherein the step of heating creates an amplification mixture in fused droplets, wherein the amplification mixture includes primers for amplifying a nucleic acid target, a probe for the nucleic acid target, and a polymerase, and wherein the amplification mixture is capable of amplifying the nucleic acid target, if present, in the fused droplets.

14. The method of claim 13, further comprising a step of collecting data from a label of the probe, and a step of determining a concentration of the nucleic acid target based on the collected data.

15. The method of claim 8, wherein the step of detecting fluorescence includes a step of detecting fluorescence test signals, further comprising (a) a step of detecting code signals from the fused droplets and (b) a step of utilizing the code signals to correlate test signals with the first and second types of reagent droplets.

\* \* \* \* \*